(12) United States Patent
Kandimalla et al.

(10) Patent No.: US 7,884,197 B2
(45) Date of Patent: Feb. 8, 2011

(54) SYNTHETIC AGONISTS OF TLR9

(75) Inventors: Ekambar Kandimalla, Southboro, MA (US); Mallikarjuna Putta, Burlington, MA (US); Dong Yu, Westboro, MA (US); Lakshmi Bhagat, Framingham, MA (US); Daqing Wang, Bedford, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/954,726

(22) Filed: Dec. 12, 2007

(65) Prior Publication Data

US 2008/0292648 A1 Nov. 27, 2008

Related U.S. Application Data

(60) Provisional application No. 60/869,604, filed on Dec. 12, 2006.

(51) Int. Cl.
| | |
|---|---|
| C07H 21/02 | (2006.01) |
| C07H 21/04 | (2006.01) |
| C12Q 1/68 | (2006.01) |
| C12N 5/00 | (2006.01) |
| C12N 5/02 | (2006.01) |
| A61K 49/00 | (2006.01) |
| A61K 31/70 | (2006.01) |
| A01N 43/04 | (2006.01) |

(52) U.S. Cl. ................... 536/23.1; 435/6; 435/375; 424/9.2; 514/44 R

(58) Field of Classification Search ............... 536/23.4, 536/24.5
See application file for complete search history.

(56) References Cited

U.S. PATENT DOCUMENTS

| | | | |
|---|---|---|---|
| 2003/0138413 A1 | 7/2003 | Vicari et al. | |
| 2005/0026861 A1* | 2/2005 | Kandimalla et al. | ........... 514/44 |
| 2006/0241076 A1 | 10/2006 | Uhlmann et al. | |

OTHER PUBLICATIONS

Kandimalla et al. "Agonists of Toll-Like Receptor 9: Modulation of host immune responses with synthetic oligodeoxynucleotides" in: Rich, Tina, Toll and Toll-Like Receptors: An immunologic Perspective (Eurekah.com and Kluwer Academic/Plenum Publishers, 2005), pp. 181-212.*
Suzuki et al. "Lipomome-encapsulated CpG oligodeoxynucleotides as a potent adjuvant for inducing type 1 innate immunity"; Cancer Research, (2004), 64:8754-8760.
Cooper et al. "CPG7909, an immunostimulatory TLR9 agonist oligodeoxynucleotide, as adjuvant to Engerix-B(R) HBV vaccine in healtht adults; A double-blind phase I/II study"; Journal of Clinical Immunology, (2004), 24(6):693-701.
Krieg "Therapeutic potential of toll-like receptor 9 activation"; Nature Review Drug Discovery, (2006), 5:471-484.
Hornung et al., "Quantitative Expression of Toll-Like Receptor 1-10 mRNA in Cellular Subsets of Human Peripheral Blood Mononuclear Cells and Sensitivity to CpG Oligodeoxynucleotides", J. Immunol., 168:4531-4537 (2002).
Poltorak et al., "Defective LPS Signaling in C3H/Hej and C57BL/10ScCr Mice: Mutations in Tlr4 Gene", Science, 282:2085-2088 (1998).
Underhill et al., "The Toll-Like Receptor 2 is Recruited to Macrophage Phagosomes and Discriminates Between Pathogens", Nature, 401:811-815 (1999).
Hayashi et al., "The Innate Immune Response to Bacterial Flagellin is Mediated by Toll-Like Receptor 5", Nature, 410:1099-1103 (2001).
Zhang et al., "A Toll-Like Receptor That Prevents Infection by Uropathogenic Bacteria", Science, 303:1522-1526 (2004).
Meier et al., "Toll-Like Receptor (TLR) 2 and TLR4 are Essential for Aspergillus-Induced Activation of Murine Macrophages", Cell. Microbiol., 5(8):561-570 (2003).
Campos et al., "Activation of Toll-Like Receptor-2 by Glycosylphosphatidylinositol Anchors from a Protozoan Parasite", J. Immunol., 167:416-423 (2001).
Hoebe et al., "Identification of Lps2 as a key Transducer of MyD88-Independent TIR Signaling", Nature, 424:743-748 (2003).
Lund et al., "Toll-Like Receptor 9-mediated Recognition of Herpes Simplex Virus-2 by Plasmacytoid Dendritic Cells", J. Exp. Med., 198(3):513-520 (2003).
Heil et al., "Species-Specific Recognition of Single-Stranded RNA Via Toll-Like Receptor 7 and 8", Science, 303:1526-1529 (2004).
Diebold et al., "Innate Antiviral Responses by means of TLR7-Mediated Recognition of Single-Stranded RNA", Science, 303:1529-1531 (2004).
Hornung et al., "Replication-Dependent Potent IFN-α Induction in Human Plasmacytoid Dendritic Cells by a Single-Stranded RNA Virus", J. Immunol., 173:5935-5943 (2004).
Akira et al., "Toll-Like Receptors: Critical Proteins Linking Innate and Acquired Immunity", Nature Immunol. 2 (8):675-680 (2001).
Medzhitov, R., "Toll-Like Receptors and Innate Immunity", Nature Rev. Immunol., 1:135-145 (2001).
Hemmi et al., "A Toll-Like Receptor Recognizes Bacterial DNA", Nature, 408:740-745 (2000).
Zhao et al., "Effect of Different Chemically Modified Oligodeoxynucleotides on Immune Stimulation", Biochem Pharmacol., 51:173-182 (1996).

(Continued)

*Primary Examiner*—Dana Shin
(74) *Attorney, Agent, or Firm*—Wayne A. Keown; Preti Flaherty

(57) ABSTRACT

The invention provides novel oligonucleotide-based compounds that individually provide distinct immune response profiles through their interactions as agonists with TLR9. The TLR9 agonists according to the invention are characterized by specific and unique chemical modifications, which provide their distinctive immune response activation profiles.

5 Claims, No Drawings

OTHER PUBLICATIONS

Zhao et al., "Modulation of Oligonucleotide-Induced Immune Stimulation by Cyclodextrin Analogs", Biochem. Pharmacol., 52:1537-1544 (1996).

Zhao et al., "Pattern and Kinetics of Cytokine Production Following Administration of Phosphorothioate Oligonucleotides in Mice", Antisense Nucleic Acid Drug Dev., 7:495-502 (1997).

Zhao et al., "Site of Chemical Modifications in CpG Containing Phosphorothioate Oligodeoxynucleotide Modulates Its Immunostimulatory Activity", Bioorg. Med. Chem. Lett., 9:3453-3458 (1999).

Zhao et al., "Immunostimulatory Activity of CpG Containing Phosphorothioate Oligodeoxynucleotide is Modulated by modification of a Single Deoxynucleoside", Bioorg. Med. Chem. Lett., 10:1051-1054 (2000).

Yu et al., "Accessible 5'-End of CpG-Containing Phosphorothioate Oligodeoxynucleotides is Essential for Immunostimulatory Activity", Bioorg. Med. Chem. Lett., 10:2585-2588 (2000).

Yu et al., "Modulation of Immunostimulatory Activity of CpG Oligonucleotides by Site-Specific Deletion of Nucleobases", Bioorg. Med. Chem. Lett., 11:2263-2267 (2001).

Kandimalla et al., "Effect of Chemical Modifications of Cytosine and Guanine in a CpG-Motif of Oligonucleotides: Structure-Immunostimulatory Activity Relationships", Bioorg. Med. Chem., 9:807-813 (2001).

Smith et al., "Trends in Reported Incidence of Primary Malignant Brain Tumors in Children in the United States", J. Natl. Cancer Inst., 90:1269-1277 (1998).

Damiano et al., "Novel Toll-Like Receptor 9 Agonist Induces Epidermal Growth Factor Receptor (EGFR) Inhibition and Synergistic Antitumor Activity with EGFR Inhibitors", Clin, Cancer Res., 12(2):577-583 (2006).

Kandimalla et al., "Immunomodulatory Oligonucleotides Containing a Cytosine-Phosphate-2'-Deoxy-7- Deazaguanosine Motif as Potent Toll-Like Receptor 9 Agonists", Proc. Natl. Acad. Sci., 102(19):6925-6930 (2005).

Kandimalla et al., "A Dinucleotide Motif in Oligonucleotides Shows Potent Immunomodulatory Activity and Overrides Species-Specific Recognition Observed with CpG Motif", Proc. Natl. Acad. Sci. USA, 100:14303-14308 (2003).

Cong et al., "Self-Stabilized CpG DNAs Optimally Activate Human B Cells and Plasmacytoid Dendritic Cells", Biochem. Biophys. Res. Commun., 310:1133-1139 (2003).

Kandimalla et al., "Secondary Structures in CpG Oligonucleotides Affect Immunostimulatory Activity", Biochem. Biophys. Res. Commun., 306:948-953 (2003).

Kandimalla et al., "Divergent Synthetic Nucleotide Motif Recognition Patters: Design and Development of Potent Immunomodulatory Oligodeoxyribonucleotide Agents with Distinct Cytokine Induction Profiles", Nuc. Acids Res., 31 (19):2393-2400 (2003).

Yu et al., "Requirement of Nucleobase Proximal to CpG Dinucleotide for Immunostimulatory Activity of Synthetic CpG DNA", Bioorg. Med. Chem., 11:459-464 (2003).

Bhagat et al., "CpG Penta- and Hexadeoxyribonucleotides as Potent Immunomodulatory Agents", Biochem. Biophys. Res. Commun., 300:853-861 (2003).

Yu et al., "Immunomers—Novel 3'-3'-Linked CpG Oligodeoxyribonucleotides as Potent Immunomodulatory Agents", Nuc. Acids Res., 30(20):4460-4469 (2002).

Yu et al., "Design, Synthesis, and Immunostimulatory Properties of CpG DNAs Containing Alkyl-Linker Substitutions: Role of Nucleosides in the Flanking Sequences", J. Med. Chem., 45:4540-4548 (2002).

Yu et al., "Potent CpG Oligonucleotides Containing Phosphodiester Linkages: in Vitro and In Vivo Immunostimulatory Properties", Biochem. Biophys. Res. Commun., 297:83-90 (2002).

Kandimalla et al., "Conjugation of Ligands at the 5'-End of CpG DNA Affects Immunostimulatory Activity", Bioconjug. Chem., 13:966-974 (2002).

Yu et al., "Immunostimulatory Properties of Phosphorothioate CpG DNA Containing Both 3'-5'-and 2'-5'-Internucleotide Linkages", Nuc. Acids Res., 30(7):1613-1619 (2002).

Yu et al., "Immunostimulatory Activity of CpG Oligonucleotides Containing Non-Ionic Methylphosphonate Linkages", Bioorg. Med. Chem., 9:2803-2808 (2001).

Putta et al., "Novel Oligodeoxynucleotide Agonists of TLR9 Containing N3-Me-dC or N1-Me-dG Modifications", Nuc. Acids Res., 34(11):3231-3238 (2006).

Zhao et al., "Effect of Different Chemically Modified Oligodeoxynucleotides on Immune Stimulation", Biochem. Pharmacol., 51:173-182 (1996).

Branda et al., "Immune Stimulation by an Antisense Oligomer Complementary to the rev Gene of HIV-1", Biochem. Pharmacol., 45(10):2037-2043 (1993).

* cited by examiner

```
                        SEQUENCE LISTING

<160> NUMBER OF SEQ ID NOS: 97

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 1
tcagtcntta c                                                              11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 2
tctgtcntta g                                                              11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 3
cagtcnttca g                                                              11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 4
tctgtcnttt t                                                              11

<210> SEQ ID NO 5
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 5
tctgtcnttg t                                                          11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 6
tagtcntttt t                                                          11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 7
tggtcnttct t                                                          11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 8
tagtcnttgt a                                                          11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG
```

```
<400> SEQUENCE: 9
tagtcnttct c                                                        11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG

<400> SEQUENCE: 10
tcntcnttct t                                                        11

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 7-deaza-dG

<400> SEQUENCE: 11
tcntacntac n                                                        11

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG
<220> FEATURE:
<221> NAME/KEY: modified_ base
<222> LOCATION: (9)
<223> OTHER INFORMATION: 7-deaza-dG

<400> SEQUENCE: 12
tcntcnacna t                                                        11

<210> SEQ ID NO 13
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 7-deaza-dG

<400> SEQUENCE: 13
tcnatcnatc n                                                             11

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 14
tcagacntta c                                                             11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 15
tctgacntta g                                                             11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 16
cagacnttca g                                                             11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_ base
<222> LOCATION: (7)
<223> OTHER INFORMATION: 7-deaza-dG

<400> SEQUENCE: 17
tctgacnttt t                                                                                        11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 18
tctgacnttg t                                                                                        11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 19
tagacntttt t                                                                                        11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 20
tggacnttct t                                                                                        11

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 7-deaza-dG

<400> SEQUENCE: 21
tagacnttgt a                                                                                        11

```
<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 22
tagacnttct c                                                          11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 23
tcntcnttct t                                                          11

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 24
tcagtcntta c                                                          11

<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 25
tctgtcntta g                                                          11

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_ base
<222> LOCATION: (6)
<223> OTHER INFORMATION: AraG

<400> SEQUENCE: 26
cagtcnttca g                                                              11

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: AraG

<400> SEQUENCE: 27
tctgtcnttt t                                                              11

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: AraG

<400> SEQUENCE: 28
tctgtcnttg t                                                              11

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: AraG

<400> SEQUENCE: 29
tagtcntttt t                                                              11

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: AraG

<400> SEQUENCE: 30
tggtcnttct t                                                              11

<210> SEQ ID NO 31
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG

<400> SEQUENCE: 31 tagtcnttgta                                                                 11

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG

<400> SEQUENCE: 32
tagtcnttct c                                                                11

<210> SEQ ID NO 33
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (6)
<223> OTHER INFORMATION: AraG

<400> SEQUENCE: 33
tcntcnttct t                                                                11

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (7)
<223> OTHER INFORMATION: AraG
<220> FEATURE:
<221> NAME/KEY: modified_base
<222> LOCATION: (11)
<223> OTHER INFORMATION: AraG

<400> SEQUENCE: 34
tcntacntac n                                                                11
```

```
<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (6)
<223> OTHER INFORMATION: AraG
<220> FEATURE:
<221> NAME/KEY: modified_base
<222> LOCATION: (9)
<223> OTHER INFORMATION: AraG

<400> SEQUENCE: 35
tcntcnacna t                                                            11

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (7)
<223> OTHER INFORMATION: AraG
<220> FEATURE:
<221> NAME/KEY: modified_base
<222> LOCATION: (11)
<223> OTHER INFORMATION: AraG

<400> SEQUENCE: 36
tcnatcnatc n                                                            11

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tctgtcgttc t                                                            11

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 38
tctgacnttc t                                                            11
```

```
<210> SEQ ID NO 39
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 7-deaza-dG

<400> SEQUENCE: 39
tcnaacnttc n                                                          11

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG

<400> SEQUENCE: 40
tcntcnttct g                                                          11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 41
tcagtngtta g                                                          11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 42
```

```
tctgtngttc t                                                     11
```

<210> SEQ ID NO 43
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
tcgttg                                                            6
```

<210> SEQ ID NO 44
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
tcgttg                                                            6
```

<210> SEQ ID NO 45
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG

<400> SEQUENCE: 45

```
tcnttg                                                            6
```

<210> SEQ ID NO 46
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
tcgttg                                                            6
```

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (11)
<223> OTHER INFORMATION: 7-deaza-dG

<400> SEQUENCE: 47
tcnaacnttc n                                                                11

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 7-deaza-dG

<400> SEQUENCE: 48
tcnaacnttc n                                                                11

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (18)
<223> OTHER INFORMATION: 7-deaza-dG

<400> SEQUENCE: 49
tctgacnttc ttctgacntt ct                                                    22

<210> SEQ ID NO 50
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: N1-Me-dG

<400> SEQUENCE: 50
tctgtcnttc t                                                                11

<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)

<223> OTHER INFORMATION: N1-Me-dG

<400> SEQUENCE: 51
tctgacnttc t                                                              11

<210> SEQ ID NO 52
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_ base
<222> LOCATION: (7)
<223> OTHER INFORMATION: N1-Me-dG

<400> SEQUENCE: 52
tctgtnnttc t                                                              11

<210> SEQ ID NO 53
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tctgacgttc t                                                              11

<210> SEQ ID NO 54
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 54
tctgacnttc t                                                              11

<210> SEQ ID NO 55
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 55
tctgtcnttc t                                                              11

<210> SEQ ID NO 56
<211> LENGTH: 11
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 56
tctgacnttc t                                                              11

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 57
tctgtcnttc t                                                              11

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 7-deaza-dG

<400> SEQUENCE: 58
tcnaacnttc n                                                              11

<210> SEQ ID NO 59
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 59
tcagtcntta g                                                              11

<210> SEQ ID NO 60
<211> LENGTH: 11
<212> TYPE: DNA
<213> ORGANISM: Artificial Sequence
<220> FEATURE:
<223> OTHER INFORMATION: Description of Combined DNA/RNA Molecule:
```

```
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 2'-O-methylribonucleotide

<400> SEQUENCE: 60
tctgtcnttc u                                                           11

<210> SEQ ID NO 61
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (10)..(11)
<223> OTHER INFORMATION: 2'-O-methylribonucleotide
<220> FEATURE:
<221> NAME/KEY: misc_feature
<222> LOCATION: (10)..(11)
<223> OTHER INFORMATION: phosphodiester linkage

<400> SEQUENCE: 61
tctgtcnttc u                                                           11

<210> SEQ ID NO 62
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: AraG
<220> FEATURE:
<221> NAME/KEY: modified_ base
<222> LOCATION: (10)..(11)
<223> OTHER INFORMATION: 2'-O-methylribonucleotide

<400> SEQUENCE: 62
tctgtcnttc u                                                           11

<210> SEQ ID NO 63
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

```
          oligonucleotide
<220> FEATURE:
<221> NAME/KEY: modified_ base
<222> LOCATION: (6)
<223> OTHER INFORMATION: AraG
<220> FEATURE:
<221> NAME/KEY: modified_ base
<222> LOCATION: (10)..(11)
<223> OTHER INFORMATION: 2'-O-methylribonucleotide

<400> SEQUENCE: 63
ctgtcnttcu c                                                          11

<210> SEQ ID NO 64
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (10)..(11)
<223> OTHER INFORMATION: 2'-O-methylribonucleotide

<400> SEQUENCE: 64
tcnaacnttc g                                                          11

<210> SEQ ID NO 65
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 7-deaza-dG

<400> SEQUENCE: 65
tcnaacnttc n                                                          11

<210> SEQ ID NO 66
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG
```

```
<220> FEATURE:
<221> NAME/KEY: modified_base
<222> LOCATION: (11)
<223> OTHER INFORMATION: 2'-O-methylribonucleotide

<400> SEQUENCE: 66
tctgtcnttc u                                                               11

<210> SEQ ID NO 67
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (10)..(11)
<223> OTHER INFORMATION: 2'-O-methylribonucleotide
<220> FEATURE:
<221> NAME/KEY: misc_feature
<222> LOCATION: (10)..(11)
<223> OTHER INFORMATION: phosphodiester linkage

<400> SEQUENCE: 67
tctgtcnttc u                                                               11

<210> SEQ ID NO 68
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG
<220> FEATURE:
<221> NAME/KEY: modified_base
<222> LOCATION: (10)..(11)
<223> OTHER INFORMATION: 2'-O-methylribonucleotide

<400> SEQUENCE: 68
tctgtcnttc u                                                               11

<210> SEQ ID NO 69
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG
<220> FEATURE:
<221> NAME/KEY: modified_base
<222> LOCATION: (10)..(11)
```

-continued

<223> OTHER INFORMATION: 2'-O-methylribonucleotide

<400> SEQUENCE: 69
ctgtcnttcu c                                                              11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (10)..(11)
<223> OTHER INFORMATION: 2'-O-methylribonucleotide

<400> SEQUENCE: 70
tcnaacnttc g                                                              11

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (11)
<223> OTHER INFORMATION: 7-deaza-dG

<400> SEQUENCE: 71
tcnaacnttc n                                                              11

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 72
tctgtcntta g                                                              11

<210> SEQ ID NO 73
<211> LENGTH: 11
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 73
cagtcnttca g                                                          11

<210> SEQ ID NO 74
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG
<220> FEATURE:
<221> NAME/KEY: modified_base
<222> LOCATION: (9)
<223> OTHER INFORMATION: 7-deaza-dG

<400> SEQUENCE: 74
tcntcnacna t                                                          11

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (10)..(11)
<223> OTHER INFORMATION: 2'-O-methylribonucleotide

<400> SEQUENCE: 75
tcagtcntta c                                                          11

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG
<220> FEATURE:
<221> NAME/KEY: misc_feature
<222> LOCATION: (3)..(4)
<223> OTHER INFORMATION: phosphodiester linkage
<220> FEATURE:
<221> NAME/KEY: misc_feature
<222> LOCATION: (5)..(6)
<223> OTHER INFORMATION: phosphodiester linkage

<400> SEQUENCE: 76
```
tcagtcntta c                                                            11

<210> SEQ ID NO 77
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (1)
<223> OTHER INFORMATION: 2'-O-methylribonucleotide
<220> FEATURE:
<221> NAME/KEY: modified_ base
<222> LOCATION: (6)
<223> OTHER INFORMATION: 7-deaza-dG

<400> SEQUENCE: 77 cagtcnttac                                                              10

<210> SEQ ID NO 78
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG
<220> FEATURE:
<221> NAME/KEY: misc_feature
<222> LOCATION: (10)..(11)
<223> OTHER INFORMATION: phosphodiester linkage

<400> SEQUENCE: 78
tcagtcntta c                                                            11

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (6)
<223> OTHER INFORMATION: AraG
<220> FEATURE:
<221> NAME/KEY: misc_feature
<222> LOCATION: (4)..(5)
<223> OTHER INFORMATION: phosphodiester linkage

<400> SEQUENCE: 79
tagtcntttt t                                                            11

<210> SEQ ID NO 80
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(6)
<223> OTHER INFORMATION: phosphodiester linkage
<220> FEATURE:

```
<221> NAME/KEY: modified_ base
<222> LOCATION: (7)
<223> OTHER INFORMATION: AraG

<400> SEQUENCE: 80
tctgtcnttg t                                                          11

<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (3)..(4)
<223> OTHER INFORMATION: phosphodiester linkage
<220> FEATURE:
<221> NAME/KEY: misc_feature
<222> LOCATION: (4)..(5)
<223> OTHER INFORMATION: phosphodiester linkage
<220> FEATURE:
<221> NAME/KEY: modified_ base
<222> LOCATION: (6)
<223> OTHER INFORMATION: AraG

<400> SEQUENCE: 81
tagtcntttt t                                                          11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: AraG
<220> FEATURE:
<221> NAME/KEY: misc_feature
<222> LOCATION: (3)..(4)
<223> OTHER INFORMATION: phosphodiester linkage
<220> FEATURE:
<221> NAME/KEY: misc_feature
<222> LOCATION: (4)..(5)
<223> OTHER INFORMATION: phosphodiester linkage
<220> FEATURE:
<221> NAME/KEY: modified_ base
<222> LOCATION: (6)
<223> OTHER INFORMATION: AraG
<220> FEATURE:
<221> NAME/KEY: misc_feature
<222> LOCATION: (7)..(8)
<223> OTHER INFORMATION: phosphodiester linkage
<220> FEATURE:
<221> NAME/KEY: modified_ base
<222> LOCATION: (9)
<223> OTHER INFORMATION: AraG

<400> SEQUENCE: 82
tcntcnacna t                                                          11

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_ base
<222> LOCATION: (3)
<223> OTHER INFORMATION: AraG
<220> FEATURE:
<221> NAME/KEY: misc_feature
<222> LOCATION: (4)..(5)
<223> OTHER INFORMATION: phosphodiester linkage
<220> FEATURE:
<221> NAME/KEY: misc_feature
<222> LOCATION: (5)..(6)
<223> OTHER INFORMATION: phosphodiester linkage
<220> FEATURE:
<221> NAME/KEY: modified_ base
<222> LOCATION: (7)
<223> OTHER INFORMATION: AraG
<220> FEATURE:
<221> NAME/KEY: misc_feature
<222> LOCATION: (7)..(8)
<223> OTHER INFORMATION: phosphodiester linkage
<220> FEATURE:
<221> NAME/KEY: misc_feature
<222> LOCATION: (8)..(9)
<223> OTHER INFORMATION: phosphodiester linkage
<220> FEATURE:
<221> NAME/KEY: modified_ base
<222> LOCATION: (11)
<223> OTHER INFORMATION: AraG

<400> SEQUENCE: 83
tcnatcnatc n                                                          11

<210> SEQ ID NO 84
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(6)
<223> OTHER INFORMATION: phosphodiester linkage
<220> FEATURE:
<221> NAME/KEY: modified_ base
<222> LOCATION: (7)
<223> OTHER INFORMATION: AraG

<400> SEQUENCE: 84
tcagtcntta c                                                          11

<210> SEQ ID NO 85
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (4)..(5)
<223> OTHER INFORMATION: phosphodiester linkage
<220> FEATURE:
<221> NAME/KEY: misc_feature
<222> LOCATION: (5)..(6)
<223> OTHER INFORMATION: phosphodiester linkage
<220> FEATURE:
<221> NAME/KEY: modified_ base
<222> LOCATION: (7)
<223> OTHER INFORMATION: AraG

<400> SEQUENCE: 85 tctgtcntag                                                            10
```

```
<210> SEQ ID NO 86
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG

<400> SEQUENCE: 86 tcntcnttt                                                                 9

<210> SEQ ID NO 87
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG

<400> SEQUENCE: 87 tcntcnttt                                                                 9

<210> SEQ ID NO 88
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (5)
<223> OTHER INFORMATION: 7-deaza-dG

<400> SEQUENCE: 88 tcncnttt                                                                  8

<210> SEQ ID NO 89
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG
```

```
<400> SEQUENCE: 89 tcntcnttt                                                              9

<210> SEQ ID NO 90
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG

<400> SEQUENCE: 90 tcntcnttt                                                              9

<210> SEQ ID NO 91
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
<223> OTHER INFORMATION: 7-deaza-dG
<220> FEATURE:
<221> NAME/KEY: modified_ base
<222> LOCATION: (6)
<223> OTHER INFORMATION: 7-deaza-dG

<400> SEQUENCE: 91 tcntcntt                                                               8

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (2)
<223> OTHER INFORMATION: 2'-O-methylribonucleotide
<220> FEATURE:
<221> NAME/KEY: modified_ base
<222> LOCATION: (7)
<223> OTHER INFORMATION: 7-deaza-dG

<400> SEQUENCE: 92
tcagtcntta c                                                          11

<210> SEQ ID NO 93
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG
```

```
<400> SEQUENCE: 93
tctgtcnttc t                                                              11

<210> SEQ ID NO 94
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG

<400> SEQUENCE: 94
tctgtcnaca g                                                              11

<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (7)
<223> OTHER INFORMATION: 7-deaza-dG
<220> FEATURE:
<221> NAME/KEY: modified_ base
<222> LOCATION: (10)..(11)
<223> OTHER INFORMATION: 2'-O-methylribonucleotide

<400> SEQUENCE: 95
tctgtcnaca g                                                              11

<210> SEQ ID NO 96
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (4)..(5)
<223> OTHER INFORMATION: phosphodiester linkage
<220> FEATURE:
<221> NAME/KEY: misc_feature
<222> LOCATION: (5)..(6)
<223> OTHER INFORMATION: phosphodiester linkage
<220> FEATURE:
<221> NAME/KEY: modified_ base
<222> LOCATION: (7)
<223> OTHER INFORMATION: AraG

<400> SEQUENCE: 96
tctgtcntta g                                                              11

<210> SEQ ID NO 97
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_ base
<222> LOCATION: (3)
```

```
-continued
<223> OTHER INFORMATION: 7-deaza-dG
<220> FEATURE:
<221> NAME/KEY: modified_ base
<222> LOCATION: (6)
<223> OTHER INFORMATION: 7-deaza-dG

<400> SEQUENCE: 97 tcntcnttt                                                          9
```

SYNTHETIC AGONISTS OF TLR9

RELATED APPLICATIONS

This application claims the benefit of U.S. Provisional Application Ser. No. 60/869,604, filed on Dec. 12, 2006, the contents of which are incorporated herein by reference.

BACKGROUND OF THE INVENTION

1. Field of the Invention

The invention relates to synthetic chemical compositions that are useful for modulation of Toll-Like Receptor (TLR)-mediated immune responses. In particular, the invention relates to agonists of Toll-Like Receptor 9 (TLR9) that generate unique cytokine and chemokine profiles.

2. Summary of the Related Art

Toll-like receptors (TLRs) are present on many cells of the immune system and have been shown to be involved in the innate immune response (Hornung, V. et al, (2002) J. Immunol. 168:4531-4537). In vertebrates, this family consists of eleven proteins called TLR1 to TLR11, which are known to recognize pathogen associated molecular patterns from bacteria, fungi, parasites, and viruses (Poltorak, a. et al. (1998) Science 282:2085-2088; Underhill, D. M., et al. (1999) Nature 401:811-815; Hayashi, F. et. al (2001) Nature 410: 1099-1103; Zhang, D. et al. (2004) Science 303:1522-1526; Meier, A. et al. (2003) Cell. Microbiol. 5:561-570; Campos, M. A. et al. (2001) J. Immunol. 167: 416-423; Hoebe, K. et al. (2003) Nature 424: 743-748; Lund, J. (2003) J. Exp. Med. 198:513-520; Heil, F. et al. (2004) Science 303:1526-1529; Diebold, S. S., et al. (2004) Science 303:1529-1531; Hornung, V. et al. (2004) J. Immunol. 173:5935-5943).

TLRs are a key means by which vertebrates recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). Some TLRs are located on the cell surface to detect and initiate a response to extracellular pathogens and other TLRs are located inside the cell to detect and initiate a response to intracellular pathogens.

TLR9 is known to recognize unmethylated CpG motifs in bacterial DNA and in synthetic oligonucleotides. (Hemmi, H. et al. (2000) Nature 408:740-745). Other modifications of CpG-containing phosphorothioate oligonucleotides can also affect their ability to act as modulators of immune response through TLR9 (see, e.g., Zhao et al., Biochem. Pharmacol. (1996) 51:173-182; Zhao et al. (1996) Biochem Pharmacol. 52:1537-1544; Zhao et al. (1997) Antisense Nucleic Acid Drug Dev. 7:495-502; Zhao et al (1999) Bioorg. Med. Chem. Lett. 9:3453-3458; Zhao et al. (2000) Bioorg. Med. Chem. Lett. 10:1051-1054; Yu, D. et al. (2000) Bioorg. Med. Chem. Lett. 10:2585-2588; Yu, D. et al. (2001) Bioorg. Med. Chem. Lett. 11:2263-2267; and Kandimalla, E. et al. (2001) Bioorg. Med. Chem. 9:807-813). Naturally occurring agonists of TLR9 have been shown to produce anti-tumor activity (e.g. tumor growth and angiogenesis) resulting in an effective anti-cancer response (e.g. anti-leukemia) (Smith, J. B. and Wickstrom, E. (1998) J. Natl. Cancer Inst. 90:1146-1154). In addition, TLR9 agonists have been shown to work synergistically with other known anti-tumor compounds (e.g. cetuximab, irinotecan) (Vincenzo, D., et al. (2006) Clin. Cancer Res. 12(2):577-583).

Certain TLR9 agonists are comprised of 3'-3' linked DNA structures containing a core CpR dinucleotide, wherein the R is a modified guanosine (U.S. patent application Ser. No. 10/279,684). In addition, specific chemical modifications have allowed the preparation of specific oligonucleotide analogs that generate distinct modulations of the immune response. In particular, structure activity relationship studies have allowed identification of synthetic motifs and novel DNA-based compounds that generate specific modulations of the immune response and these modulations are distinct from those generated by unmethylated CpG dinucleotides. (Kandimalla, E. et al. (2005) Proc. Natl. Acad. Sci. USA 102:6925-6930. Kandimalla, E. et al. (2003) Proc. Nat. Acad. Sci. USA 100:14303-14308; Cong, Y. et al. (2003) Biochem Biophys Res. Commun. 310:1133-1139; Kandimalla, E. et al. (2003) Biochem. Biophys. Res. Commun. 306:948-953; Kandimalla, E. et al. (2003) Nucleic Acids Res. 31:2393-2400; Yu, D. et al. (2003) Bioorg. Med. Chem. 11:459-464; Bhagat, L. et al. (2003) Biochem. Biophys. Res. Commun. 300:853-861; Yu, D. et al. (2002) Nucleic Acids Res. 30:4460-4469; Yu, D. et al. (2002) J. Med. Chem. 45:4540-4548. Yu, D. et al. (2002) Biochem. Biophys. Res. Commun. 297:83-90; Kandimalla. E. et al. (2002) Bioconjug. Chem. 13:966-974; Yu, D. et al. (2002) Nucleic Acids Res. 30:1613-1619; Yu, D. et al. (2001) Bioorg. Med. Chem. 9:2803-2808; Yu, D. et al. (2001) Bioorg. Med. Chem. Lett. 11:2263-2267; Kandimalla, E. et al. (2001) Bioorg. Med. Chem. 9:807-813; Yu, D. et al. (2000) Bioorg. Med. Chem. Lett. 10:2585-2588; Putta, M. et al. (2006) Nucleic Acids Res. 34:3231-3238).

The inventors have surprisingly discovered that unique modifications to the sequence flanking the core CpR dinucleotide produce novel agonists of TLR9 that generate distinct cytokine and chemokine profiles in vitro and in vivo. This ability to "custom-tune" the cytokine and chemokine response to a CpR containing oligonucleotide promises to provide the ability to prevent and/or treat various disease conditions in a disease-specific and even a patient-specific manner. Thus, there is a need for new oligonucleotide analog compounds to provide such custom-tuned responses.

BRIEF SUMMARY OF THE INVENTION

The invention provides novel oligonucleotide-based compounds that individually provide distinct immune response profiles through their interactions as agonists with TLR9. The TLR9 agonists according to the invention are characterized by specific and unique chemical modifications, which provide their distinctive immune response activation profiles.

The TLR9 agonists according to the invention induce immune responses in various cell types and in various in vitro and in vivo experimental models, with each agonist providing a distinct immune response profile. As such, they are useful as tools to study the immune system, as well as to compare the immune systems of various animal species, such as humans and mice. The TLR9 agonists according to the invention are also useful in the prevention and/or treatment of various diseases, either alone, in combination with other drugs, or as adjuvants for antigens used as vaccines.

Thus, in a first aspect, the invention provides oligonucleotide-based agonists of TLR9.

In a second aspect, the invention provides a composition comprising an oligonucleotide-based TLR9 agonist ("a compound") according to the invention and a physiologically acceptable carrier.

In a third aspect, the invention provides a vaccine. Vaccines according to this aspect comprise a composition according to the invention, and further comprise an antigen.

In a fourth aspect, the invention provides methods for generating a TLR9-mediated immune response in a vertebrate, such methods comprising administering to the vertebrate a compound, composition or vaccine according to the invention.

In a fifth aspect, the invention provides methods for therapeutically treating a patient having a disease or disorder, such methods comprising administering to the patient a compound, composition or vaccine according to the invention.

In a sixth aspect, the invention provides methods for preventing a disease or disorder, such methods comprising administering to the patient a compound, composition or vaccine according to the invention.

DETAILED DESCRIPTION OF THE PREFERRED EMBODIMENTS

The invention provides novel oligonucleotide-based compounds that individually provide distinct immune response profiles through their interactions as agonists with TLR9. The TLR9 agonists according to the invention are characterized by unique chemical modifications, which provide their distinctive immune response activation profiles. All publications cited herein reflect the level of skill in the art and are hereby incorporated by reference in their entirety. Any conflict between the teachings of these references and this specification shall be resolved in favor of the latter.

The TLR9 agonists according to the invention induce immune responses in various cell types and in various in vivo and in vitro experimental models, with each agonist providing a distinct immune response profile. As such, they are useful as tools to study the immune system, as well as to compare the immune systems of various animal species, such as humans and mice. The TLR9 agonists according to the invention are also useful in the prevention and/or treatment of various diseases, either alone, in combination with other drugs, or as adjuvants for antigens used as vaccines.

Certain TLR9 agonists according to the invention are shown in Table I below. In this table, the oligonucleotide-based TLR9 agonists have all phosphorothioate (PS) linkages, except where indicated. Except where indicated, all nucleotides are deoxyribonucleotides. Those skilled in the art will recognize, however, that phosphodiester (PO) linkages, or a mixture of PS and PO linkages can be used.

TABLE I

| Seq. ID. No./ Oligo No. | Sequence and Modifications |
|---|---|
| 1 | 5'-TCAGTCG1TTAC-X-CATTG1CTGACT-5' |
| 2 | 5'-TCTGTCG$_1$TTAG-X-GATTG$_1$CTGTCT-5' |
| 3 | 5'-CAGTCG$_1$TTCAG-X-GACTTG$_1$CTGAC-5' |
| 4 | 5'-TCTGTCG$_1$TTTT-X-TTTTG$_1$CTGTCT-5' |
| 5 | 5'-TCTGTCG$_1$TTGT-X-TGTTG$_1$CTGTCT-5' |
| 6 | 5'-TAGTCG$_1$TTTTT-X-TTTTTG$_1$CGTAT-5' |
| 7 | 5'-TGGTCG$_1$TTCTT-X-TTCTTG$_1$CTGGT-5' |
| 8 | 5'-TAGTCG$_1$TTGTA-X-ATGTTG$_1$CTGAT-5' |
| 9 | 5'-TAGTCG$_1$TTCTC-X-CTCTTG$_1$CTGAT-5' |
| 10 | 5'-TCG$_1$TCG$_1$TTCTT-X-TTCTTG$_1$CTGCT-5' |
| 11 | 5'-TCG$_1$TACG$_1$TACG$_1$-X-G$_1$CATG$_1$CATG$_1$CT-5' |
| 12 | 5'-TCG$_1$TCG$_1$ACG$_1$AT-X-TAG$_1$CAG$_1$CTG$_1$CT-5' |

TABLE I-continued

| Seq. ID. No./ Oligo No. | Sequence and Modifications |
|---|---|
| 13 | 5'-TCG$_1$ATCG$_1$ATCG$_1$-X-G$_1$CTAG$_1$CTAG$_1$CT-5' |
| 14 | 5'-TCAGACG$_1$TTAC-X-CATTG$_1$CAGACT-5' |
| 15 | 5'-TCTGACG$_1$TTAG-X-GATTG$_1$CAGTCT-5' |
| 16 | 5'-CAGACG$_1$TTCAG-X-GACTTG$_1$CAGAC-5' |
| 17 | 5'-TCTGACG$_1$TTTT-X-TTTTG$_1$CAGTCT-5' |
| 18 | 5'-TCTGACGTTGT-X-TGTTG$_1$CAGTCT-5' |
| 19 | 5'-TAGACG$_1$TTTTT-X-TTTTTG$_1$CAGAT-5' |
| 20 | 5'-TGGACG$_1$TTCTT-X-TTCTTG$_1$CAGGT-5' |
| 21 | 5'-TAGACGTTGTA-X-ATGTTG$_1$CAGAT-5' |
| 22 | 5'-TAGACG$_1$TTCTC-X-CTCTTG$_1$CAGAT-5' |
| 23 | 5'-TCG$_1$TCG$_1$TTCTT-X-TTCTTG$_1$CTG$_1$CT-5' |
| 24 | 5'-TCAGTCG$_2$TTAC-X-CATTG$_2$CTGACT-5' |
| 25 | 5'-TCTGTCG$_2$TTAG-X-GATTG$_2$CTGTCT-5' |
| 26 | 5'-CAGTCG$_2$TTCAG-X-GACTTG$_2$CTGAC-5' |
| 27 | 5'-TCTGTCG$_2$TTTT-X-TTTTG$_2$CTGTCT-5' |
| 28 | 5'-TCTGTCG$_2$TTGT-X-TGTTG$_2$CTGTCT-5' |
| 29 | 5'-TAGTCG$_2$TTTTT-X-TTTTTG$_2$CGTAT-5' |
| 30 | 5'-TGGTCG$_2$TTCTT-X-TTCTTG$_2$CTGGT-5' |
| 31 | 5'-TAGTCG$_2$TGTA-X-ATGTTG$_2$CTGAT-5' |
| 32 | 5'-TAGTCG$_2$TTCTC-X-CTCTTG$_2$CTGAT-5' |
| 33 | 5'-TCG$_2$TCG$_2$TTCTT-X-TTCTTG$_2$CTG$_2$CT-5' |
| 34 | 5'-TCG$_2$TACG$_2$TACG$_2$-X-G$_2$CATG$_2$CATG$_2$CT-5' |
| 35 | 5'-TCG$_2$TCG$_2$ACG$_2$AT-X-TAG$_2$CAG$_2$CTG$_2$CT-5' |
| 36 | 5'-TCG$_2$ATCG$_2$ATCG$_2$-X-G$_2$CTAG$_2$CTAG$_2$CT-5' |
| 37 | 5'-TCTGTCGTTCT-Y-TCTTGCTGTCT-5' |
| 38 | 5'-TCTGACG$_1$TTCT-Y-TCTTG$_1$CAGTCT-5' |
| 39 | 5'-TCG$_1$AACG$_1$TTCG$_1$-Y-G$_1$CTTG$_1$CAAG$_1$CT-5' |
| 40 | 5'-TCG$_1$TCG$_1$TTCTG-Y-GTCTTG$_1$CTG$_1$CT-5' |
| 41 | 5'-TCAGTC$_1$GTTAG-Y-GATTGC$_1$TGACT-5' |
| 42 | 5'-TCTGTC$_1$GTTCT-Y-TCTTGC$_1$TGTCT-5' |
| 43 | 5'-TCGTTGL-Y-LGTTGCT-5' |
| 44 | 5'-TCGTTGM-Y-MGTTGCT-5' |
| 45 | 5'-TCG$_1$TTGM-Y-MGTTG$_1$CT-5' |
| 46 | 5'-TCGTTGM-X-MGTTGCT-5' |
| 47 & 93 | 5'-TCG$_1$AACG$_1$TTCG$_1$-M-TCTTG$_1$CTGTCT-5' |
| 48 & 94 | 5'-TCG$_1$AACG$_1$TTCG$_1$-M-GACAG$_1$CTGTCT-5' |
| 49 | [(5'-TCTGACG$_1$TTCT)$_2$Y]$_2$Y |
| 50 | 5'-TCTGTCG$_3$TTCT-Y-TCTTG$_3$CTGTCT-5' |

TABLE I-continued

| Seq. ID. No./ Oligo No. | Sequence and Modifications |
|---|---|
| 51 | 5'-TCTGACG$_3$TTCT-Y-TCTTG$_3$CAGTCT-5' |
| 52 | 5'-TCTGTC$_1$G$_3$TTCT-Y-TCTTG$_3$C$_1$TGTCT-5' |
| 53 | 5'-TCTGACGTTCT-Z-TCTTGCAGTCT-5' |
| 54 | 5'-TCTGACG$_1$TTCT-Z-TCTTG$_1$CAGTCT-5' |
| 55 | 5'-TCTGTCG$_1$TTCT-Z-TCTTG$_1$CTGTCT-5' |
| 56 | 5'-TCTGACG$_1$TTCT-S-TCTTG$_1$CAGTCT-5' |
| 57 | 5'-TCTGTCG$_1$TTCT-S-TCTTG$_1$CTGTCT-5' |
| 58 | 5'-TCG$_1$AACG$_1$TTCG$_1$-S-G$_1$CTTG$_1$CAAG$_1$CT-5' |
| 59 | 5'-TCAGTCG$_1$TTAG-S-GATTG$_1$CTGACT-5' |
| 60 | 5'-TCTGTCG$_1$TTCU̲o-X-oU̲CTTG$_1$CTGTCT-5' |
| 61 | 5'-TCTGTCG$_1$TTC̲oU̲o-X-oU̲oC̲TTG$_1$CTGTCT-5' |
| 62 | 5'-TCTGTCG$_2$TTC̲U̲-X-U̲C̲TTG$_2$CTGTCT-5' |
| 63 | 5'-CTGTCG$_2$TTCU̲C̲-X-C̲U̲CTTG$_2$CTGTC-5' |
| 64 | 5'-TCG$_1$AACG$_1$TTC̲G̲-X-G̲C̲TTG$_1$CAAG$_1$CT-5' |
| 65 & 95 | 5'-TCG$_1$AACG$_1$TTCG$_1$-L-G̲A̲CAG$_1$CTGTCT-5' |
| 66 | 5'-TCTGTCG$_1$TTCU̲o-X-oU̲CTTG$_1$CTGCTC-5' |
| 67 | 5'-TCTGTCG$_1$TTC̲oU̲o-X-oU̲oC̲TTG$_1$CTGCTC-5' |
| 68 | 5'-TCTGTCG$_2$TTC̲U̲-X-U̲C̲TTG$_2$CTGCTC-5' |
| 69 | 5'-CTGTCG$_2$TTCU̲C̲-X-C̲U̲CTTG$_2$CTGCTC-5' |
| 70 | 5'-TCG$_1$AACG$_1$TTC̲G̲-X-G̲C̲TTG$_1$CAAG$_1$CT-5' |
| 71 & 95 | 5'-TCG$_1$AACG$_1$TTCG$_1$-L-G̲A̲CAG$_1$CTGTCT-5' |
| 72 | 5'-TCTGTCG$_1$TTAG-S-GATTG$_1$CTGTCT-5' |
| 73 | 5'-CAGTCG$_1$TTCAG-Z-GACTTG$_1$CTGAC-5' |
| 74 | 5'-TCG$_1$TCG$_1$ACG$_1$AT-S-TAG$_1$CAG$_1$CTG$_1$CT-5' |
| 75 | 5'-TCAGTCG$_1$TTA̲C̲-X-C̲A̲TTG$_1$CTGACT-5' |
| 76 | 5'-TCAoGToCG$_2$TTAC-X-CATTG$_2$CoTGoACT-5' |
| 77 | 5'-U̲CAGTCG$_1$TTAC-X-CATTG$_1$CTGACU̲-5' |
| 78 | 5'-TCAGTCG$_1$TTAoC-X-CoATTG$_1$CTGACT-5' |
| 79 | 5'-TAGToCG$_2$TTTTT-X-TTTTTG$_2$CoTGTAT-5' |
| 80 | 5'-TCTGToCG$_2$TTGT-X-TGTTG$_2$CoTGTCT-5' |
| 81 | 5'-TAGoToCG$_2$TTTTT-X-TTTTTG$_2$CoToGTAT-5' |
| 82 | 5'-TCG$_2$oToCG$_2$AoCG$_2$AT-X-TAG$_2$CoAG$_2$CoToG$_2$CT-5' |
| 83 | 5'-TCG$_2$AoToCG$_2$oAoTCG$_2$-X-G$_2$CToAoG$_2$CoToAG$_2$CT-5' |
| 84 | 5'-TCAGToCG$_2$TTAC-S-CATTG$_2$CoTGACT-5' |
| 85 & 95 | 5'-TCTGToCG$_2$TAG-Z-GATTG$_2$CoToGTCT-5' |
| 86 | 5'-TCG$_1$TCG$_1$TTTL-S-LTTTG$_1$CTG$_1$CT-5' |
| 87 & 97 | 5'-LTCG$_1$TCG$_1$TTTL-S-LTTTG$_1$CTG$_1$CTL-5' |
| 88 | 5'-TCG$_1$CG$_1$TTTL-Z-LTTTG$_1$CTG$_1$CT-5' |
| 89 | 5'-LTCG$_1$TCG$_1$TTTL-Z-LTTTG$_1$CTG$_1$CTL-5' |
| 90 | 5'-TCG$_1$TCG$_1$TTTL-X-LTTTG$_1$CTG$_1$CT-5' |
| 91 | 5'-LTCG$_1$TCG$_1$TTL-X-LTTTG$_1$CTG$_1$CTL-5' |
| 92 | 5'-TC̲AGTCG$_1$TTAC-X-CATTG$_1$CTGAC̲T-5' |

G$_1$ = 7-deaza-dG;
G$_2$ = AraG;
G$_3$ = N$^1$-Me-dG;
C$_1$ = 1-(2'-deoxy-β-D-ribofuranosyl)-2-oxo-7-deaza-8-methyl-purine;
U̲/C̲/G̲/A̲ = 2'-O-methylribonucleotides;
o = phosphodiester linkage;
X = Glycerol;
Y = 1,3,5-Pentanetriol;
L = 1,3-Propanediol;
M = 1,5-Pentanediol;
Z = cis,cis-1,3,5-Cyclohexanetriol;
S = 3-Me-1,3,5-pentanetriol Exemplar TLR9 agonists from Table I were tested for immune stimulatory activity in HEK293 cells expressing TLR9, as described in Example 2. The results shown in Table II(a), II(b), II(c), and II(d) below demonstrate that specific chemical modifications to 3'-3' linked oligonucleotides will alter their TLR9 mediated NF-kB activation profile 24 hours after administration. More generally, these data demonstrate that specific chemical modifications to 3'-3' linked oligonucleotides can be used to increase or decrease NF-kB activation.

TABLE II(a)

NF-kB Activation Profiles in HEK293 Cells Expressing TLR9

| Seq. ID. No./ Oligo No. | Sequences and Modification (5'-3') | Fold Changes in NF-kB Activity ± SD at 10 μg/ml |
|---|---|---|
| 1 | 5'-TCAGTCG$_1$TTAC-X-CATTG$_1$CTGACT-5' | 13.94 ± 0.33 |
| 2 | 5'-TCTGTCG$_1$TTAG-X-GATTG$_1$CTGTCT-5' | 6.76 ± 0.12 |
| 3 | 5'-CAGTCG$_1$TTCAG-X-GACTTG$_1$CTGAC-5' | 10.45 ± 0.13 |
| 4 | 5'-TCTGTCG$_1$TTTT-X-TTTTG$_1$CTGTCT-5' | 7.84 ± 0.02 |
| 5 | 5'-TCTGTCG$_1$TTGT-X-TGTTG$_1$CTGTCT-5' | 9.45 ± 1.31 |
| 6 | 5'-TAGTCG$_1$TTTTT-X-TTTTTG$_1$CGTAT-5' | 6.95 ± 0.05 |
| 7 | 5'-TGGTCG$_1$TTCTT-X-TTCTTG$_1$CTGGT-5' | 5.02 ± 0.13 |
| 8 | 5'-TAGTCG$_1$TTGTA-X-ATGTTG$_1$CTGAT-5' | 2.75 ± 0.46 |
| 9 | 5'-TAGTCG$_1$TTCTC-X-CTCTTG$_1$CTGAT-5' | 12.59 ± 0.26 |

TABLE II(a)-continued

NF-kB Activation Profiles in HEK293 Cells Expressing TLR9

| Seq. ID. No./ Oligo No. | Sequences and Modification (5'-3') | Fold Changes in NF-kB Activity ± SD at 10 µg/ml |
|---|---|---|
| 10 | 5'-TCG$_1$TCG$_1$TTCTT-X-TTCTTG$_1$CTG$_1$CT-5' | 13.24 ± 1.58 |
| 14 | 5'-TCAGACG$_1$TTAC-X-CATTG$_1$CAGACT-5' | 14.32 ± 0.19 |
| 15 | 5'-TCTGACG$_1$TTAG-X-GATTG$_1$CAGTCT-5' | 12.19 ± 0.94 |
| 16 | 5'-CAGACG$_1$TTCAG-X-GACTTG$_1$CAGAC-5' | 16.42 ± 0.44 |
| 17 | 5'-TCTGACG$_1$TTTT-X-TTTTG$_1$CAGTCT-5' | 16.49 ± 1.13 |
| 18 | 5'-TCTGACG$_1$TTGT-X-TGTTG$_1$CAGTCT-5' | 14.63 ± 0.03 |
| 19 | 5'-TAGACG$_1$TTTTT-X-TTTTTG$_1$CAGAT-5' | 16.06 ± 0.71 |
| 20 | 5'-TGGACG$_1$TTCTT-X-TTCTTG$_1$CAGGT-5' | 13.28 ± 0.42 |
| 21 | 5'-TAGACG$_1$TTGTA-X-ATGTTG$_1$CAGAT-5' | 11.75 ± 0.42 |
| 22 | 5'-TAGACG$_1$TTCTC-X-CTCTTG$_1$CAGAT-5' | 13.70 ± 0.21 |
| Media | | 1 ± 0.07 |

TABLE II(b)

NF-kB Activation Profiles in HEK293 Cells Expressing TLR9

| Seq. ID. No./ Oligo No. | Sequences and Modification (5'-3') | Fold Changes in NF-kB Activity at 10 µg/ml |
|---|---|---|
| 37 | 5'-TCTGTCGTTCT-Y-TCTTGCTGTCT-5' | 11.35 |
| 38 | 5'-TCTGACG$_1$TTCT-Y-TCTTG$_1$CAGTCT-5' | 11.51 |
| 50 | 5'-TCTGTCG$_3$TTCT-Y-TCTTG$_3$CTGTCT-5' | 12.32 |
| 52 | 5'-TCTGTCG$_3$TTCT-Y-TCTTG$_3$CTGTCT-5' | 9.40 |
| 57 | 5'-TCTGTCG$_1$TTCT-S-TCTTG$_1$CTGTCT-5' | 11.05 |
| PBS | | 1.00 |

TABLE II(c)

NF-kB Activation Profiles in HEK293 Cells Expressing TLR9

| Seq. ID. No./ Oligo No. | Sequences and Modification (5'-3') | Fold Changes in NF-κB Activity ± SD at 10 µg/ml |
|---|---|---|
| 60 | 5'-TCTGTCG$_1$TTCUo-X-oUCTTG$_1$CTGTCT-5' | 11.2 ± 0.06 |
| 61 | 5'-TCTGTCG$_1$TTCoUo-X-oUoCTTG$_1$CTGTCT-5' | 9.5 ± 0.06 |
| 62 | 5'-TCTGTCG$_2$TTCU-X-UCTTG$_2$CTGTCT-5' | 6.6 ± 0.04 |
| 63 | 5'-CTGTCG$_2$TTCUC-X-CUCTTG$_2$CTGTC-5' | 14.6 ± 0.09 |
| 64 | 5'-TCG$_1$AACG$_1$TTCG-X-GCTTG$_1$CAAG$_1$CT-5' | 32.1 ± 0.6 |
| 65 & 95 | 5'-TCG$_1$AACG$_1$TTCG$_1$-L-GACAG$_1$CTGTCT-5' | 23.7 ± 0.2 |
| PBS | | 1 ± 0.03 |

TABLE II(d)

NF-kB Activation Profiles in HEK293 Cells Expressing TLR9

| Seq. ID. No./ Oligo No. | Sequences and Modification (5'-3') | Fold Changes in NF-κB Activity ± SD at 10 µg/ml |
|---|---|---|
| 72 | 5'-TCTGTCG$_1$TTAG-S-GATTG$_1$CTGTCT-5' | 3.81 ± 0.14 |
| 73 | 5'-CAGTCG$_1$TTCAG-Z-GACTTG$_1$CTGAC-5' | 5.47 ± 0.17 |
| 74 | 5'-TCG$_1$TCG$_1$ACG$_1$AT-S-TAG$_1$CAG$_1$CTG$_1$CT-5' | 9.46 ± 1.35; 9.18 ± 0.09 |
| 75 | 5'-TCAGTCG$_1$TTAC-X-CATTG$_1$CTGACT-5' | 5.08 ± 0.58; 6.91 ± 1.52 |
| 77 | 5'-UCAGTCG$_1$TTAC-X-CATTG$_1$CTGACU-5' | 5.33 ± 0.25; 4.85 ± 0.46 |
| 78 | 5'-TCAGTCG$_1$TTAoC-X-CoATTG$_1$CTGACT-5' | 7.63 ± 0.54; 10.7 ± 90.9 |
| 79 | 5'-TAGToCG$_2$TTTTT-X-TTTTTG$_2$CoTGTAT-5' | 5.63 ± 1.46; 5.75 ± 0.45 |
| 80 | 5'-TCTGToCG$_2$TTGT-X-TGTTG$_2$CoTGTCT-5' | 9.60 ± 1.39; 9.75 ± 0.25 |
| 81 | 5'-TAGoToCG$_2$TTTTT-X-TTTTTG$_2$CoToGTAT-5' | 5.63 ± 0.46; 6.22 ± 0.12 |
| 82 | 5'-TCG$_2$oToCG$_2$AoCG$_2$AT-X-TAG$_2$CoAG$_2$CoToG$_2$CT-5' | 9.71 ± 0.75; 12.5 ± 90.3 |
| 83 | 5'-TCG$_2$AoToCG$_2$oAoTCG$_2$-X-G$_2$CToAoG$_2$CoToAG$_2$CT-5' | 7.24 ± 0.42 |
| 84 | 5'-TCAGToCG$_2$TTAC-S-CATTG$_2$CoTGACT-5' | 8.92 ± 0.88; 10.33 ± 0.2; 12.16 ± 1.5 |

TABLE II(d)-continued

NF-kB Activation Profiles in
HEK293 Cells Expressing TLR9

| Seq. ID. No./ Oligo No. | Sequences and Modification (5'-3') | Fold Changes in NF-κB Activity ± SD at 10 µg/ml |
|---|---|---|
| 85 & 96 | 5'-TCTGoToCG$_2$TAG-Z-GATTG$_2$CoToGTCT-5' | 9.13 ± 1.25; 8.05 ± 0.39; 11.3 ± 40.3 |
| 86 | 5'-TCG$_1$TCG$_1$TTTL-S-LTTTG$_1$CTG$_1$CT-5' | 11.6 ± 10.6 |
| 88 | 5'-TCG$_1$CG$_1$TTTL-Z-LTTTG$_1$CTG$_1$CT-5' | 9.61 ± 0.14; 9.32 ± 0.20 |
| 89 | 5'-LTCG$_1$TCG$_1$TTTL-Z-LTTTG$_1$CTG$_1$CTL-5' | 2.57 ± 0.28 |
| 90 | 5'-TCG$_1$TCG$_1$TTTL-X-LTTTG$_1$CTG$_1$CT-5' | 9.65 ± 1.78; 9.57 ± 0.18 |
| 92 | 5'-T<u>C</u>AGTCG$_1$TTAC-X-CATTG$_1$CTGA<u>C</u>T-5' | 5.67 ± 0.25; 7.25 ± 1.23 |
| Media | | 1.0 ± 0.17; 1 ± 0.25; 1.0 ± 0.02; 1.0 ± 0.11 |

Exemplar TLR9 agonists from Table I were tested for immune stimulatory activity in the C57BL/6 mouse spleenocyte IL-12 assay, as described in Example 3. The results shown in Table III(a), III(b) and III(c) below demonstrate that specific chemical modifications to 3'-3' linked oligonucleotides will alter their TLR9 mediated IL-12 activation profile in spleen cells 24 hours after administration and that this activation profile may be dose dependent depending on the chemical modification. More generally, these data demonstrate that specific chemical modifications to 3'-3' linked oligonucleotides can be used to increase or decrease IL-12 activation.

TABLE III(a)

Induction of IL-12 Secretion in C57BL/6 Mouse Spleen Cell Cultures

| Seq. ID. No./ Oligo No. | Sequences and Modification (5'-3') | IL-12 (pg/m ± SD1) at 1 µg/ml | at 3 µg/ml |
|---|---|---|---|
| 1 | 5'-TCAGTCG$_1$TTAC-X-CATTG$_1$CTGACT-5' | 733 ± 5 | 638 ± 14 |
| 2 | 5'-TCTGTCG$_1$TTAG-X-GATTG$_1$CTGTCT-5' | 919 ± 8 | 660 ± 8 |
| 3 | 5'-CAGTCG$_1$TTCAG-X-GACTTG$_1$CTGAC-5' | 500 ± 26 | 634 ± 49 |
| 4 | 5'-TCTGTCG$_1$TTTT-X-TTTTG$_1$CTGTCT-5' | 822 ± 9 | 516 ± 7 |
| 5 | 5'-TCTGTCG$_1$TTGT-X-TGTTG$_1$CTGTCT-5' | 636 ± 6 | 369 ± 4 |
| 6 | 5'-TAGTCG$_1$TTTTT-X-TTTTTG$_1$CGTAT-5' | 857 ± 0 | 115 ± 0 |
| 7 | 5'-TGGTCG$_1$TTCTT-X-TTCTTG$_1$CTGGT-5' | 61 ± 0 | 357 ± 16 |
| 8 | 5'-TAGTCG$_1$TTGTA-X-ATGTTG$_1$CTGAT-5' | 253 ± 10 | 120 ± 13 |
| 9 | 5'-TAGTCG$_1$TTCTC-X-CTCTTG$_1$CTGAT-5' | 743 ± 33 | 553 ± 12 |
| 10 | 5'-TCG$_1$TCG$_1$TTCTT-X-TTCTTG$_1$CTG$_1$CT-5' | 714 ± 0 | 913 ± 12 |
| 14 | 5'-TCAGACG$_1$TTAC-X-CATTG$_1$CAGACT-5' | 1654 ± 64 | 1592 ± 27 |
| 15 | 5'-TCTGACG$_1$TTAG-X-GATTG$_1$CAGTCT-5' | 1299 ± 2 | 1257 ± 8 |
| 16 | 5'-CAGACG$_1$TTCAG-X-GACTTG$_1$CAGAC-5' | 1152 ± 11 | 1134 ± 0 |
| 17 | 5'-TCTGACG$_1$TTTT-X-TTTTG$_1$CAGTCT-5' | 1370 ± 4 | 1015 ± 7 |
| 18 | 5'-TCTGACG$_1$TTGT-X-TGTTG$_1$CAGTCT-5' | 1140 ± 16 | 816 ± 4 |
| 19 | 5'-TAGACG$_1$TTTTT-X-TTTTTG$_1$CAGAT-5' | 1215 ± 32 | 719 ± 3 |
| 20 | 5'-TGGACG$_1$TTCTT-X-TTCTTG$_1$CAGGT-5' | 814 ± 9 | 645 ± 40 |
| 21 | 5'-TAGACG$_1$TTGTA-X-ATGTTG$_1$CAGAT-5' | 835 ± 34 | 750 ± 16 |

TABLE III(a)-continued

Induction of IL-12 Secretion in C57BL/6 Mouse Spleen Cell Cultures

| Seq. ID. No./ | | IL-12 (pg/m ± SD1) | |
|---|---|---|---|
| Oligo No. | Sequences and Modification (5'-3') | at 1 µg/ml | at 3 µg/ml |
| 22 | 5'-TAGAC$G_1$TTCTC-X-CTCTT$G_1$CAGAT-5' | 1211 ± 26 | 898 ± 24 |
| Media | | 154 ± 1 | 154 ± 1 |

TABLE III(b)

Induction of IL-12 Secretion in C57BL/6 Mouse Spleen Cell Cultures

| Seq. ID. No./ Oligo No. | Sequences and Modifications (5'-3') | IL-12 (pg/ml ± SD) | |
|---|---|---|---|
| 24 | 5'-TCAGTC$G_2$TTAC-X-CATT$G_2$CTGACT-5' | 932 ± 18 | 892 ± 2 |
| 25 | 5'-TCTGTC$G_2$TTAG-X-GATT$G_2$CTGTCT-5' | 771 ± 6 | 604 ± 6 |
| 26 | 5'-CAGTC$G_2$TTCAG-X-GACTT$G_2$CTGAC-5' | 835 ± 4 | 905 ± 4 |
| 27 | 5'-TCTGTC$G_2$TTTT-X-TTTT$G_2$CTGTCT-5' | 571 ± 11 | 502 ± 2 |
| 28 | 5'-TCTGTC$G_2$TTGT-X-TGTT$G_2$CTGTCT-5' | 567 ± 0 | 698 ± 77 |
| 29 | 5'-TAGTC$G_2$TTTTT-X-TTTTT$G_2$CGTAT-5' | 975 ± 24 | 656 ± 33 |
| 30 | 5'-TGGTC$G_2$TTCTT-X-TTCTT$G_2$CTGGT-5' | 426 ± 16 | 393 ± 1 |
| 31 | 5'-TAGTC$G_2$TTGTA-X-ATGTT$G_2$CTGAT-5' | 568 ± 23 | 575 ± 14 |
| 32 | 5'-TAGTC$G_2$TTCTC-X-CTCTT$G_2$CTGAT-5' | 960 ± 2 | 647 ± 13 |
| 33 | 5'-TC$G_2$TC$G_2$TTCTT-X-TTCTT$G_2$CT$G_2$CT-5' | 659 ± 10 | 1014 ± 1 |
| 34 | 5'-TC$G_2$TAC$G_2$TAC$G_2$-X-$G_2$CAT$G_2$CAT$G_2$CT-5' | 1044 ± 66 | 1109 ± 32 |
| 35 | 5'-TC$G_2$TC$G_2$AC$G_2$AT-X-TA$G_2$CA$G_2$CT$G_2$CT-5' | 1406 ± 36 | 968 ± 4 |
| 36 | 5'-TC$G_2$ATC$G_2$ATC$G_2$-X-$G_2$CTA$G_2$CTA$G_2$CT-5' | 912 ± 3 | 1035 ± 11 |
| media | | 190 ± 4 | |

TABLE III(c)

Induction of IL-12 Secretion in C57BL/6 Mouse Spleen Cell Cultures

| Seq. ID. No./ Oligo No. | Sequences and Modification (5'-3') | IL-12 (pg/ml ± SD) |
|---|---|---|
| 72 | 5'-TCTGTC$G_1$TTAG-S-GATT$G_1$CTGTCT-5' | 988 ± 224 |
| 73 | 5'-CAGTC$G_1$TTCAG-Z-GACTT$G_1$CTGAC-5' | 504 ± 76 |
| 74 | 5'-TC$G_1$TC$G_1$AC$G_1$AT-S-TA$G_1$CA$G_1$CT$G_1$CT-5' | 906 ± 47 |
| 75 | 5'-TCAGTC$G_1$TTAC-X-CATT$G_1$CTGACT-5' | 473 ± 67 |
| 77 | 5'-UCAGTC$G_1$TTAC-X-CATT$G_1$CTGACU-5' | 265 ± 19 |
| 78 | 5'-TCAGTC$G_1$TTAoC-X-CoATT$G_1$CTGACT-5' | 833 ± 63 |
| 79 | 5'-TAGToC$G_2$TTTTT-X-TTTTT$G_2$CoTGTAT-5' | 380 ± 54 |
| 80 | 5'-TCTGToC$G_2$TTGT-X-TGTT$G_2$CoTGTCT-5' | 1502 ± 162 |

TABLE III(c)-continued

Induction of IL-12 Secretion in C57BL/6 Mouse Spleen Cell Cultures

| Seq. ID. No./ Oligo No. | Sequences and Modification (5'-3') | IL-12 (pg/ml ± SD) |
|---|---|---|
| 81 | 5'-TAG$o$T$o$CG$_2$TTTTT-X-TTTTTG$_2$C$o$T$o$GTAT-5' | 370 ± 47 |
| 82 | 5'-TCG$_2o$T$o$CG$_2$A$o$CG$_2$AT-X-TAG$_2$C$o$AG$_2$C$o$T$o$G$_2$CT-5' | 1599 ± 156 |
| 83 | 5'-TCG$_2$A$o$T$o$CG$_2o$A$o$TCG$_2$-X-G$_2$CT$o$A$o$G$_2$C$o$T$o$AG$_2$CT-5' | 1203 ± 109 |
| 84 | 5'-TCAGT$o$CG$_2$TTAC-S-CATTG$_2$C$o$TGACT-5' | 838 ± 61 |
| 85 & 96 | 5'-TCTG$o$T$o$CG$_2$TAG-Z-GATTG$_2$C$o$T$o$GTCT-5' | 589 ± 45 |
| 86 | 5'-TCG$_1$TCG$_1$TTTL-S-LTTTG$_1$CTG$_1$CT-5' | 1603 ± 167 |
| 88 | 5'-TCG$_1$CG$_1$TTTL-Z-LTTTG$_1$CTG$_1$CT-5' | 1643 ± 40 |
| 89 | 5'-LTCG$_1$TCG$_1$TTTL-Z-LTTTG$_1$CTG$_1$CTL-5' | 450 ± 50 |
| 90 | 5'-TCG$_1$TCG$_1$TTTL-X-LTTTG$_1$CTG$_1$CT-5' | 1393 ± 9 |
| 92 | 5'-TCAGTCG$_1$TTAC-X-CATTG$_1$CTGACT-5' | 383 ± 23 |
| Media | | 82 ± 4; 168 ± 15 |

Exemplar TLR9 agonists from Table I were tested for immune stimulatory activity in the C57BL/6 mouse spleenocyte IL-6 assay, as described in Example 3. The results shown in Table IV(a), IV(b), and IV(c) below demonstrate that specific chemical modifications to 3'-3' linked oligonucleotides will alter their TLR9 mediated IL-6 activation profile in spleen cells 24 hours after administration and that this activation profile may be dose dependent depending on the chemical modification. More generally, these data demonstrate that specific chemical modifications to 3'-3' linked oligonucleotides can be used to increase or decrease IL-6 activation.

TABLE IV(a)

Induction of IL-6 Secretion in C57BL/6 Mouse Spleen Cell Cultures

| Seq. ID. No./ Oligo No. | Sequences and Modification (5'-3') | IL-6 (pg/ml ± SD) | |
|---|---|---|---|
| | | at 1 µg/ml | at 3 µg/ml |
| 1 | 5'-TCAGTCG$_1$TTAC-X-CATTG$_1$CTGACT-5' | 2436 ± 93 | 6282 ± 138 |
| 2 | 5'-TCTGTCG$_1$TTAG-X-GATTG$_1$CTGTCT-5' | 1812 ± 95 | 5758 ± 55 |
| 3 | 5'-CAGTCG$_1$TTCAG-X-GACTTG$_1$CTGAC-5' | 1650 ± 63 | 3349 ± 46 |
| 4 | 5'-TCTGTCG$_1$TTTT-X-TTTTG$_1$CTGTCT-5' | 707 ± 59 | 7018 ± 3 |
| 5 | 5'-TCTGTCG$_1$TTGT-X-TGTTG$_1$CTGTCT-5' | 1302 ± 56 | 5874 ± 83 |
| 6 | 5'-TAGTCG$_1$TTTTT-X-TTTTTG$_1$CGTAT-5' | 1025 ± 93 | 1677 ± 12 |
| 7 | 5'-TGGTCG$_1$TTCTT-X-TTCTTG$_1$CTGGT-5' | 453 ± 8 | 3068 ± 3 |
| 8 | 5'-TAGTCG$_1$TTGTA-X-ATGTTG$_1$CTGAT-5' | 914 ± 74 | 1147 ± 30 |
| 9 | 5'-TAGTCG$_1$TTCTC-X-CTCTTG$_1$CTGAT-5' | 3570 ± 21 | 12114 ± 86 |
| 10 | 5'-TCG$_1$TCG$_1$TTCTT-X-TTCTTG$_1$CTG$_1$CT-5' | 77 ± 0 | 1657 ± 17 |
| 14 | 5'-TCAGACG$_1$TTAC-X-CATTG$_1$CAGACT-5' | 2605 ± 15 | 7206 ± 16 |
| 15 | 5'-TCTGACG$_1$TTAG-X-GATTG$_1$CAGTCT-5' | 1705 ± 28 | 6538 ± 63 |
| 16 | 5'-CAGACG$_1$TTCAG-X-GACTTG$_1$CAGAC-5' | 1081 ± 20 | 3765 ± 18 |
| 17 | 5'-TCTGACG$_1$TTTT-X-TTTTG$_1$CAGTCT-5' | 1711 ± 32 | 8386 ± 33 |

TABLE IV(a)-continued

Induction of IL-6 Secretion in C57BL/6 Mouse Spleen Cell Cultures

| Seq. ID. No./ Oligo No. | Sequences and Modification (5'-3') | IL-6 (pg/ml ± SD) | |
|---|---|---|---|
| | | at 1 µg/ml | at 3 µg/ml |
| 18 | 5'-TCTGAC$G_1$TTGT-X-TGTT$G_1$CAGTCT-5' | 1725 ± 0 | 7340 ± 142 |
| 19 | 5'-TAGAC$G_1$TTTTT-X-TTTTT$G_1$CAGAT-5' | 984 ± 16 | 3312 ± 22 |
| 20 | 5'-TGGAC$G_1$TTCTT-X-TTCTT$G_1$CAGGT-5' | 515 ± 77 | 1828 ± 22 |
| 21 | 5'-TAGAC$G_1$TTGTA-X-ATGTT$G_1$CAGAT-5' | 221 ± 5 | 1539 ± 9 |
| 22 | 5'-TAGAC$G_1$TTCTC-X-CTCTT$G_1$CAGAT-5' | 1593 ± 19 | 6960 ± 81 |
| Media | | 0 ± 0 | 0 ± 0 |

TABLE IV(b)

Induction of IL-6 Secretion in C57BL/6 Mouse Spleen Cell Cultures (24 hours)

| Seq. ID. No./ Oligo No. | Sequences and Modifications (5'-3') | IL-6 (pg/ml ± SD) | |
|---|---|---|---|
| 24 | 5'-TCAGTC$G_2$TTAC-X-CATT$G_2$CTGACT-5' | 8276 ± 35 | 11634 ± 83 |
| 25 | 5'-TCTGTC$G_2$TTAG-X-GATT$G_2$CTGTCT-5' | 5428 ± 106 | 11860 ± 154 |
| 26 | 5'-CAGTC$G_2$TTCAG-X-GACTT$G_2$CTGAC-5' | 6389 ± 15 | 12402 ± 77 |
| 27 | 5'-TCTGTC$G_2$TTTT-X-TTTT$G_2$CTGTCT-5' | 3977 ± 89 | 8058 ± 46 |
| 28 | 5'-TCTGTC$G_2$TTGT-X-TGTT$G_2$CTGTCT-5' | 4333 ± 59 | 10555 ± 49 |
| 29 | 5'-TAGTC$G_2$TTTTT-X-TTTTT$G_2$CGTAT-5' | 3380 ± 24 | 9348 ± 90 |
| 30 | 5'-TGGTC$G_2$TTCTT-X-TTCTT$G_2$CTGGT-5' | 2452 ± 45 | 4028 ± 15 |
| 31 | 5'-TAGTC$G_2$TTGTA-X-ATGTT$G_2$CTGAT-5' | 2574 ± 45 | 6426 ± 40 |
| 32 | 5'-TAGTC$G_2$TTCTC-X-CTCTT$G_2$CTGAT-5' | 6432 ± 4 | 10872 ± 413 |
| 33 | 5'-TC$G_2$TC$G_2$TTCTT-X-TTCTT$G_2$CT$G_2$CT-5' | 6136 ± 24 | 10408 ± 7 |
| 34 | 5'-TC$G_2$TAC$G_2$TAC$G_2$-X-$G_2$CAT$G_2$CAT$G_2$CT-5' | 7840 ± 61 | 15642 ± 56 |
| 35 | 5'-TC$G_2$TC$G_2$AC$G_2$AT-X-TA$G_2$CA$G_2$CT$G_2$CT-5' | 8004 ± 141 | 15174 ± 54 |
| 36 | 5'-TC$G_2$ATC$G_2$ATC$G_2$-X-$G_2$CTA$G_2$CTA$G_2$CT-5' | 5590 ± 259 | 14788 ± 441 |
| media | | 346 ± 0 | |

TABLE IV(c)

Induction of IL-6 Secretion in C57BL/6 Mouse Spleen Cell Cultures (24 hours)

| Seq. ID. No./ Oligo No. | Sequences and Modification (5'-3') | IL-6 (pg/ml ± SD) |
|---|---|---|
| 72 | 5'-TCTGTC$G_1$TTAG-S-GATT$G_1$CTGTCT-5' | 8388 ± 1609 |
| 73 | 5'-CAGTC$G_1$TTCAG-Z-GACTT$G_1$CTGAC-5' | 4198 ± 1602 |
| 74 | 5'-TC$G_1$TC$G_1$AC$G_1$AT-S-TA$G_1$CA$G_1$CT$G_1$CT-5' | 18828 ± 1448 |
| 75 | 5'-TCAGTC$G_1$TTAC-X-CATT$G_1$CTGACT-5' | 3689 ± 109 |

TABLE IV(c)-continued

Induction of IL-6 Secretion in C57BL/6
Mouse Spleen Cell Cultures (24 hours)

| Seq. ID. No./ Oligo No. | Sequences and Modification (5'-3') | IL-6 (pg/ml ± SD) |
|---|---|---|
| 77 | 5'-<u>U</u>CAGTCG$_1$TTAC-X-CATTG$_1$CTGAC<u>U</u>-5' | 91 ± 12 |
| 78 | 5'-TCAGTCG$_1$TTAoC-X-CoATTG$_1$CTGACT-5' | 22047 ± 8443 |
| 79 | 5'-TAGToCG$_2$TTTTT-X-TTTTTG$_2$CoTGTAT-5' | 1234 ± 508 |
| 80 | 5'-TCTGToCG$_2$TTGT-X-TGTTG$_2$CoTGTCT-5' | 1402 ± 5369 |
| 81 | 5'-TAGoToCG$_2$TTTTT-X-TTTTTG$_2$CoToGTAT-5' | 373 ± 61 |
| 82 | 5'-TCG$_2$oToCG$_2$AoCG$_2$AT-X-TAG$_2$CoAG$_2$CoToG$_2$CT-5' | 86355 ± 4638 |
| 83 | 5'-TCG$_2$AoToCG$_2$oAoTCG$_2$-X-G$_2$CToAoG$_2$CoToAG$_2$CT-5' | 10871 ± 1996 |
| 84 | 5'-TCAGToCG$_2$TTAC-S-CATTG$_2$CoTGACT-5' | 30346 ± 1670 |
| 85 & 96 | 5'-TCTGoToCG$_2$TAG-Z-GATTG$_2$CoToGTCT-5' | 113 ± 11 |
| 86 | 5'-TCG$_1$TCG$_1$TTTL-S-LTTTG$_1$CTG$_1$CT-5' | 15654 ± 470 |
| 88 | 5'-TCG$_1$CG$_1$TTTL-Z-LTTTG$_1$CTG$_1$CT-5' | 16317 ± 659 |
| 89 | 5'-LTCG$_1$TCG$_1$TTTL-Z-LTTTG$_1$CTG$_1$CTL-5' | 1259 ± 215 |
| 90 | 5'-TCG$_1$TCG$_1$TTTL-X-LTTTG$_1$CTG$_1$CT-5' | 13864 ± 344 |
| 92 | 5'-T<u>C</u>AGTCG$_1$TTAC-X-CATTG$_1$CTGA<u>C</u>T-5' | 2171 ± 186 |
| Media |  | 51 ± 3; 60 ± 1 |

Exemplar TLR9 agonists from Table I were tested for immune stimulatory activity in the human B-cell proliferation assay, as described in Example 4. The results shown in Table V(a), V(b), V(c), V(d) and V(e) below demonstrate that specific chemical modifications to 3'-3' linked oligonucleotides will alter their TLR9 mediated B-cell proliferation activity and that this activation profile may be dose dependent depending on the chemical modification. More generally, these data demonstrate that specific chemical modifications to 3'-3' linked oligonucleotides can be used to regulate B-cell proliferation.

TABLE V(a)

Human B-Cell Proliferation Assay

| Seq. ID. No./ Oligo No. | Sequences and Modification (5'-3') | [$^3$H]-T (cpm ± SD) at 1 μg/ml | at 3 μg/ml |
|---|---|---|---|
| 1 | 5'-TCAGTCG$_1$TTAC-X-CATTG$_1$CTGACT-5' | 9170 ± 5038 | 7556 ± 3260 |
| 2 | 5'-TCTGTCG$_1$TTAG-X-GATTG$_1$CTGTCT-5' | 9907 ± 4299 | 9405 ± 3319 |
| 3 | 5'-CAGTCG$_1$TTCAG-X-GACTTG$_1$CTGAC-5' | 7594 ± 4088 | 7094 ± 1526 |
| 4 | 5'-TCTGTCG$_1$TTTT-X-TTTTG$_1$CTGTCT-5' | 13130 ± 6721 | 12343 ± 4336 |
| 5 | 5'-TCTGTCG$_1$TTGT-X-TGTTG$_1$CTGTCT-5' | 11990 ± 5511 | 12102 ± 5618 |
| 6 | 5'-TAGTCG$_1$TTTTT-X-TTTTTG$_1$CGTAT-5' | 13676 ± 3676 | 14223 ± 6073 |
| 7 | 5'-TGGTCG$_1$TTCTT-X-TTCTTG$_1$CTGGT-5' | 7286 ± 2800 | 7007 ± 1424 |
| 8 | 5'-TAGTCG$_1$TTGTA-X-ATGTTG$_1$CTGAT-5' | 7858 ± 2877 | 8757 ± 3733 |
| 9 | 5'-TAGTCG$_1$TTCTC-X-CTCTTG$_1$CTGAT-5' | 7834 ± 2397 | 6840 ± 2158 |
| Media |  | 559 ± 355 | 559 ± 355 |

TABLE V(b)

Human B-Cell Proliferation Assay

| Seq. ID. No./ Oligo No. | Sequences and Modification (5'-3') | [$^3$H]-T (cpm ± SD) | |
|---|---|---|---|
| 24 | 5'-TCAGTC$G_2$TTAC-X-CATT$G_2$CTGACT-5' | 12015 ± 2721 | 22634 ± 7474 |
| 25 | 5'-TCTGTC$G_2$TTAG-X-GATT$G_2$CTGTCT-5' | 12033 ± 1502 | 28048 ± 14380 |
| 26 | 5'-CAGTC$G_2$TTCAG-X-GACTT$G_2$CTGAC-5' | 8738 ± 2957 | 23675 ± 11455 |
| 27 | 5'-TCTGTC$G_2$TTTT-X-TTTT$G_2$CTGTCT-5' | 17623 ± 4158 | 24309 ± 7340 |
| 28 | 5'-TCTGTC$G_2$TTGT-X-TGTT$G_2$CTGTCT-5' | 13631 ± 1735 | 18438 ± 3212 |
| 29 | 5'-TAGTC$G_2$TTTTT-X-TTTTT$G_2$CGTAT-5' | 12051 ± 5367 | 19867 ± 9831 |
| 30 | 5'-TGGTC$G_2$TTCTT-X-TTCTT$G_2$CTGGT-5' | 17206 ± 8474 | 18061 ± 9703 |
| 31 | 5'-TAGTC$G_2$TTGTA-X-ATGTT$G_2$CTGAT-5' | 21600 ± 10694 | 22746 ± 13411 |
| 32 | 5'-TAGTC$G_2$TTCTC-X-CTCTT$G_2$CTGAT-5' | 15827 ± 8603 | 26722 ± 16455 |
| 33 | 5'-TC$G_2$TC$G_2$TTCTT-X-TTCTT$G_2$CT$G_2$CT-5' | 19269 ± 14059 | 21945 ± 11281 |
| 34 | 5'-TC$G_2$TAC$G_2$TAC$G_2$-X-$G_2$CAT$G_2$CAT$G_2$CT-5' | 11228 ± 4499 | 17990 ± 7547 |
| 35 | 5'-TC$G_2$TC$G_2$AC$G_2$AT-X-TA$G_2$CA$G_2$CT$G_2$CT-5' | 13364 ± 2570 | 22787 ± 3265 |
| 36 | 5'-TC$G_2$ATC$G_2$ATC$G_2$-X-$G_2$CTA$G_2$CTA$G_2$CT-5' | 14071 ± 3313 | 31519 ± 2373 |
| media | | 634 ± 166 | |

TABLE V(c)

Human B-Cell Proliferation Assay

| Seq. ID. No./ Oligo No. | Sequences and Modification (5'-3') | [$^3$H]-T (cpm ± SD) | |
|---|---|---|---|
| 38 | 5'-TCTGAC$G_1$TTCT-Y-TCTT$G_1$CAGTCT-5' | 4714 ± 1043 | 4535 ± 1269 |
| 39 | 5'-TC$G_1$AAC$G_1$TTC$G_1$-Y-$G_1$CTT$G_1$CAA$G_1$CT-5' | 3664 ± 219 | 7556 ± 1615 |
| 40 | 5'-TC$G_1$TC$G_1$TTCTG-Y-GTCTT$G_1$CT$G_1$CT-5' | 4346 ± 453 | 6093 ± 2052 |
| 41 | 5'-TCAGTCGTTAG-Y-GATTGCTGACT-5' | 3585 ± 495 | 4371 ± 1380 |
| 42 | 5'-TCTGTCGTTCT-Y-TCTTGCTGTCT-5' | 5607 ± 1163 | 5202 ± 1980 |
| 43 | 5'-TCGTTGL-Y-LGTTGCT-5' | 3302 ± 359 | 4767 ± 737 |
| 47 & 93 | 5'-TC$G_1$AAC$G_1$TTC$G_1$-M-TCTT$G_1$CTGTCT-5' | 6010 ± 1951 | 6469 ± 3332 |
| 48 & 94 | 5'-TC$G_1$AAC$G_1$TTC$G_1$-M-GACA$G_1$CTGTCT-5' | 3507 ± 768 | 4351 ± 2101 |
| | PBS | 545 ± 237 | |

TABLE V(d)

Human B-Cell Proliferation Assay

| Seq. ID. No./ Oligo No. | Sequences and Modification (5'-3') | Proliferation Index at 1 μg/ml |
|---|---|---|
| 60 | 5'-TCTGTC$G_1$TTC<u>U</u>o-X-o<u>U</u>CTT$G_1$CTGTCT-5' | 28.4 |
| 61 | 5'-TCTGTC$G_1$TT<u>C</u>o<u>U</u>o-X-o<u>U</u>o<u>C</u>TT$G_1$CTGTCT-5' | 31.3 |
| 62 | 5'-TCTGTC$G_2$TT<u>CU</u>-X-<u>UC</u>TT$G_2$CTGTCT-5' | 42.6 |

TABLE V(d)-continued

Human B-Cell Proliferation Assay

| Seq. ID. No./ Oligo No. | Sequences and Modification (5'-3') | Proliferation Index at 1 µg/ml |
|---|---|---|
| 63 | 5'-CTGTCG$_2$TTCUC-X-CUCTTG$_2$CTGTC-5' | 41.5 |
| 64 | 5'-TCG$_1$AACG$_1$TTCG-X-GCTTG$_1$CAAG$_1$CT-5' | 45.6 |
| 65 & 95 | 5'-TCG$_1$AACG$_1$TTCG$_1$-L-GACAG$_1$CTGTCT-5' | 23.8 |
| Medium | | 1 |

TABLE V(e)

Human B-Cell Proliferation Assay

| Seq. ID. No./ Oligo No. | Sequences and Modification (5'-3') | Proliferation Index at 1 µg/ml |
|---|---|---|
| 66 | 5'-TCTGTCG$_1$TTCUo-X-oUCTTG$_1$CTGCTC-5' | 13582 ± 1296 |
| 67 | 5'-TCTGTCG$_1$TTCoUo-X-oUoCTTG$_1$CTGCTC-5' | 19250 ± 1860 |
| 68 | 5'-TCTGTCG$_2$TTCU-X-UCTTG$_2$CTGCTC-5' | 24809 ± 3983 |
| 69 | 5'-CTGTCG$_2$TTCUC-X-CUCTTG$_2$CTGCTC-5' | 21125 ± 2056 |
| 70 | 5'-TCG$_1$AACG$_1$TTCG-X-GCTTG$_1$CAAG$_1$CT-5' | 20306 ± 6796 |
| 71 & 95 | 5'-TCG$_1$AACG$_1$TTCG$_1$-L-GACAG$_1$CTGTCT-5' | 11547 ± 631 |
| 72 | 5'-TCTGTCG$_1$TTAG-S-GATTG$_1$CTGTCT-5' | 16603 ± 2124 |
| 73 | 5'-CAGTCG$_1$TTCAG-Z-GACTTG$_1$CTGAC-5' | 9787 ± 1290 |
| 74 | 5'-TCG$_1$TCG$_1$ACG$_1$AT-S-TAG$_1$CAG$_1$CTG$_1$CT-5' | 16934 ± 2628 |
| 80 | 5'-TCTGToCG$_2$TTGT-X-TGTTG$_2$CoTGTCT-5' | 16347 ± 980<br>18093 ± 3142 |
| 84 | 5'-TCAGToCG$_2$TTAC-S-CATTG$_2$CoTGACT-5' | 14546 ± 2616 |
| 85 & 96 | 5'-TCTGoToCG$_2$TAG-Z-GATTG$_2$CoToGTCT-5' | 10051 ± 1376 |
| 86 | 5'-TCG$_1$TCG$_1$TTTL-S-LTTTG$_1$CTG$_1$CT-5' | 18297 ± 1246 |
| 88 | 5'-TCG$_1$CG$_1$TTTL-Z-LTTTG$_1$CTG$_1$CT-5' | 12128 ± 2106<br>16534 ± 1037 |
| 89 | 5'-LTCG$_1$TCG$_1$TTTL-Z-LTTTG$_1$CTG$_1$CTL-5' | 10749 ± 1191 |
| 90 | 5'-TCG$_1$TCG$_1$TTTL-X-LTTTG$_1$CTG$_1$CT-5' | 11357 ± 692;<br>22666 ± 54 |
| 91 & 97 | 5'-LTCG$_1$TCG$_1$TTL-X-LTTTG$_1$CTG$_1$CTL-5' | |
| 92 | 5'-TCAGTCG$_1$TTAC-X-CATTG$_1$CTGACT-5' | |
| Media | | 621 ± 215 |

Exemplar TLR9 agonists from Table I were tested for immune stimulatory activity in the human PBMC and B-Cell assays for IL-1Ra, IL-6, IL-10, and IL-12, as described in Example 3. The results shown in Table VI(a), VI(b), VI(c), VI(d), VI(e), VI(f), VI(g), and VI(h) below demonstrate that specific chemical modifications to 3'-3' linked oligonucleotides will alter their TLR9 mediated IL-1Rα, IL-6, IL-10, and/or IL-12 activation profile in human PBMCs. More generally, these data demonstrate that specific chemical modifications to 3'-3' linked oligonucleotides can be used to increase or decrease IL-1Rα, IL-6, IL-10, and IL-12 activation.

TABLE VI(a)

Human PBMC Assay for IL-1Rα, IL-6 and IL-12

| Seq. ID. No./ Oligo No. | Sequences and Modification (5'-3') | IL-1Rα (pg/ml) at 10 µg/ml | IL-6 (pg/ml) at 10 µg/ml | IL-12 (pg/ml) at 10 µg/ml |
|---|---|---|---|---|
| 1 | 5'-TCAGTCG$_1$TTAC-X-CATTG$_1$CTGACT-5' | 1331 | 1035 | 116.5 |
| 2 | 5'-TCTGTCG$_1$TTAG-X-GATTG$_1$CTGTCT-5' | 599.5 | 630 | 56.5 |
| 3 | 5'-CAGTCG$_1$TTCAG-X-GACTTG$_1$CTGAC-5' | 1133 | 867.5 | 76 |
| 4 | 5'-TCTGTCG$_1$TTTT-X-TTTTG$_1$CTGTCT-5' | 926 | 994 | 81 |
| 5 | 5'-TCTGTCG$_1$TTGT-X-TGTTG$_1$CTGTCT-5' | 874.5 | 813.5 | 69 |
| 6 | 5'-TAGTCG$_1$TTTTT-X-TTTTTG$_1$CGTAT-5' | 921 | 958 | 90.5 |
| 7 | 5'-TGGTCG$_1$TTCTT-X-TTCTTG$_1$CTGGT-5' | 1365 | 1110.5 | 101.5 |
| 8 | 5'-TAGTCG$_1$TTGTA-X-ATGTTG$_1$CTGAT-5' | 744 | 1048.5 | 75.5 |
| 9 | 5'-TAGTCG$_1$TTCTC-X-CTCTTG$_1$CTGAT-5' | 1239 | 1084.5 | 104.5 |
| 10 | 5'-TCG$_1$TCG$_1$TTCTT-X-TTCTTG$_1$CTG$_1$CT-5' | 1727 | 1415.5 | 145 |
| 11 | 5'-TCG$_1$TACG$_1$TACG$_1$-X-G$_1$CATG$_1$CATG$_1$CT-5' | 2905.5 | 2099.5 | 197.5 |
| 12 | 5'-TCG$_1$TCG$_1$ACG$_1$AT-X-TAG$_1$CAG$_1$CTG$_1$CT-5' | 2965 | 1985.3 | 192.7 |
| 13 | 5'-TCG$_1$ATCG$_1$ATCG$_1$-X-G$_1$CTAG$_1$CTAG$_1$CT-5' | 3584.5 | 2543.5 | 300.5 |
| Media | | 187 | 36 | 21 |

TABLE VI(b)

Human PBMC Assay for IL-1Rα, IL-6 and IL-12

| Seq. ID. No./ Oligo No. | Sequences and Modification (5'-3') | IL-1Rα (pg/ml) at 10 µg/ml | IL-6 (pg/ml) at 10 µg/ml | IL-12 (pg/ml) at 10 µg/ml |
|---|---|---|---|---|
| 24 | 5'-TCAGTCG$_2$TTAC-X-CATTG$_2$CTGACT-5' | 10537.8 | 340.8 | 350.7 |
| 25 | 5'-TCTGTCG$_2$TTAG-X-GATTG$_2$CTGTCT-5' | 14850.4 | 413.6 | 456.1 |
| 26 | 5'-CAGTCG$_2$TTCAG-X-GACTTG$_2$CTGAC-5' | 9440.6 | 335.0 | 304.4 |
| 27 | 5'-TCTGTCG$_2$TTTT-X-TTTTG$_2$CTGTCT-5' | 13014.5 | 499.0 | 421.9 |
| 28 | 5'-TCTGTCG$_2$TTGT-X-TGTTG$_2$CTGTCT-5' | 10270.2 | 363.2 | 323.0 |
| 29 | 5'-TAGTCG$_2$TTTTT-X-TTTTTG$_2$CGTAT-5' | 11644.7 | 421.2 | 362.3 |
| 30 | 5'-TGGTCG$_2$TTCTT-X-TTCTTG$_2$CTGGT-5' | 10528.9 | 465.7 | 339.2 |
| 31 | 5'-TAGTCG$_2$TTGTA-X-ATGTTG$_2$CTGAT-5' | 19086.4 | 554.6 | 551.3 |
| 32 | 5'-TAGTCG$_2$TTCTC-X-CTCTTG$_2$CTGAT-5' | 15514.6 | 434.8 | 462.9 |

TABLE VI(b)-continued

Human PBMC Assay for IL-1Rα, IL-6 and IL-12

| Seq. ID. No./ Oligo No. | Sequences and Modification (5'-3') | IL-1Rα (pg/ml) at 10 μg/ml | IL-6 (pg/ml) at 10 μg/ml | IL-12 (pg/ml) at 10 μg/ml |
| --- | --- | --- | --- | --- |
| 33 | 5'-TCG$_2$TCG$_2$TTCTT-X-TTCTTG$_2$CTG$_2$CT-5' | 22655.8 | 551.9 | 598.6 |
| 34 | 5'-TCG$_2$TACG$_2$TACG$_2$-X-G$_2$CATG$_2$CATG$_2$CT-5' | 20375.5 | 456.3 | 596.3 |
| 35 | 5'-TCG$_2$TCG$_2$ACG$_2$AT-X-TAG$_2$CAG$_2$CTG$_2$CT-5' | 17750.6 | 383.5 | 521.9 |
| 36 | 5'-TCG$_2$ATCG$_2$ATCG$_2$-X-G$_2$CTAG$_2$CTAG$_2$CT-5' | 23576.8 | 428.0 | 706.3 |
| media | | 799.5 | 15.7 | 47.7 |

TABLE VI(c)

Human PBMC Assay for IL-6 (24 hours)

| Seq. ID. No./ Oligo No. | Sequences and Modification (5'-3') | IL-6 (pg/ml ± SD) at 10 μg/ml |
| --- | --- | --- |
| 60 | 5'-TCTGTCG$_1$TTCUo-X-oUCTTG$_1$CTGTCT-5' | 423 ± 1 |
| 61 | 5'-TCTGTCG$_1$TTCoUo-X-oUoCTTG$_1$CTGTCT-5' | 938 ± 14 |
| 62 | 5'-TCTGTCG$_2$TTCU-X-UCTTG$_2$CTGTCT-5' | 497 ± 4 |
| 63 | 5'-CTGTCG$_2$TTCUC-X-CUCTTG$_2$CTGTC-5' | 409 ± 2 |
| 64 | 5'-TCG$_1$AACG$_1$TTCG-X-GCTTG$_1$CAAG$_1$CT-5' | 474 ± 0 |
| 65 & 95 | 5'-TCG$_1$AACG$_1$TTCG$_1$-L-GACAG$_1$CTGTCT-5' | 626 ± 3 |
| Medium | | 0 ± 0 |

TABLE VI(d)

Human PBMC Assay for IL-6 (24 hours)

| Seq. ID. No./ Oligo No. | Sequences and Modification (5'-3') | IL-6 (pg/ml ± SD) at 10 μg/ml |
| --- | --- | --- |
| 66 | 5'-TCTGTCG$_1$TTCUo-X-oUCTTG$_1$CTGCTC-5' | 135.63 |
| 67 | 5'-TCTGTCG$_1$TTCoUo-X-oUoCTTG$_1$CTGCTC-5' | 117.98 |
| 68 | 5'-TCTGTCG$_2$TTCU-X-UCTTG$_2$CTGCTC-5' | 300.79 |
| 69 | 5'-CTGTCG$_2$TTCUC-X-CUCTTG$_2$CTGCTC-5' | 151.84 |
| 70 | 5'-TCG$_1$AACG$_1$TTCG-X-GCTTG$_1$CAAG$_1$CT-5' | 268.71 |
| 71 & 95 | 5'-TCG$_1$AACG$_1$TTCG$_1$-L-GACAG$_1$CTGTCT-5' | 364.23 |
| 75 | 5'-TCAGTCG$_1$TTAC-X-CATTG$_1$CTGACT-5' | 722.58 |
| 77 | 5'-UCAGTCG$_1$TTAC-X-CATTG$_1$CTGACU-5' | 615.21 |
| 78 | 5'-TCAGTCG$_1$TTAoC-X-CoATTG$_1$CTGACT-5' | 449.96 |
| 79 | 5'-TAGToCG$_2$TTTTT-X-TTTTTG$_2$CoTGTAT-5' | 658.10 |
| 80 | 5'-TCTGToCG$_2$TTGT-X-TGTTG$_2$CoTGTCT-5' | 490.37 |
| 81 | 5'-TAGoToCG$_2$TTTTT-X-TTTTTG$_2$CoToGTAT-5' | 668.52 |
| 82 | 5'-TCG$_2$oToCG$_2$AoCG$_2$AT-X-TAG$_2$CoAG$_2$CoToG$_2$CT-5' | 614.15 |

TABLE VI(d)-continued

Human PBMC Assay for IL-6 (24 hours)

| Seq. ID. No./Oligo No. | Sequences and Modification (5'-3') | IL-6 (pg/ml ± SD) at 10 µg/ml |
|---|---|---|
| 84 | 5'-TCAGToCG$_2$TTAC-S-CATTG$_2$CoTGACT-5' | 603.68; 351.00 |
| 85 & 96 | 5'-TCTGoToCG$_2$TAG-Z-GATTG$_2$CoToGTCT-5' | 387.97; 464.58 |
| 88 | 5'-TCG$_1$CG$_1$TTTL-Z-LTTTG$_1$CTG$_1$CT-5' | 440.25 |
| 90 | 5'-TCG$_1$TCG$_1$TTTL-X-LTTTG$_1$CTG$_1$CT-5' | 446.67 |
| 92 | 5'-T<u>C</u>AGTCG$_1$TTAC-X-CATTG$_1$CTGA<u>C</u>T-5' | 605.79 |
| Media | | 7.12; 3.59 |

TABLE VI(e)

Human PBMC Assay for IL-10 (24 hours)

| Seq. ID. No./Oligo No. | Sequences and Modification (5'-3') | IL-10 (pg/ml ± SD) at 10 µg/ml |
|---|---|---|
| 60 | 5'-TCTGTCG$_1$TTC<u>U</u>o-X-o<u>UC</u>TTG$_1$CTGTCT-5' | 44 ± 6 |
| 61 | 5'-TCTGTCG$_1$TT<u>C</u>o<u>U</u>o-X-o<u>U</u>o<u>C</u>TTG$_1$CTGTCT-5' | 50 ± 6 |
| 62 | 5'-TCTGTCG$_2$TT<u>CU</u>-X-<u>UC</u>TTG$_2$CTGTCT-5' | 42 ± 2 |
| 63 | 5'-CTGTCG$_2$TT<u>CU</u>C-X-<u>CU</u>CTTG$_2$CTGTC-5' | 55 ± 2 |
| 64 | 5'-TCG$_1$AACG$_1$TT<u>CG</u>-X-<u>GC</u>TTG$_1$CAAG$_1$CT-5' | 11 ± 2 |
| 65 & 95 | 5'-TCG$_1$AACG$_1$TTCG$_1$-L-<u>GA</u>CAG$_1$CTGTCT-5' | 26 ± 2 |
| Medium | | 18 ± 0 |

TABLE VI(f)

Human PBMC Assay for IL-12 (24 hours)

| Seq. ID. No./Oligo No. | Sequences and Modification (5'-3') | IL-12 (pg/ml ± SD) at 10 µg/ml |
|---|---|---|
| 66 | 5'-TCTGTCG$_1$TTC<u>U</u>o-X-o<u>UC</u>TTG$_1$CTGCTC-5' | 284.03 |
| 67 | 5'-TCTGTCG$_1$TT<u>C</u>o<u>U</u>o-X-o<u>U</u>o<u>C</u>TTG$_1$CTGCTC-5' | 296.62 |
| 68 | 5'-TCTGTCG$_2$TT<u>CU</u>-X-<u>UC</u>TTG$_2$CTGCTC-5' | 502.12 |
| 69 | 5'-CTGTCG$_2$TT<u>CU</u>C-X-<u>CU</u>CTTG$_2$CTGCTC-5' | 531.48 |
| 70 | 5'-TCG$_1$AACG$_1$TT<u>CG</u>-X-<u>GC</u>TTG$_1$CAAG$_1$CT-5' | 729.32 |
| 71 & 95 | 5'-TCG$_1$AACG$_1$TTCG$_1$-L-<u>GA</u>CAG$_1$CTGTCT-5' | 810.12 |
| 75 | 5'-TCAGTCG$_1$TT<u>AC</u>-X-<u>CA</u>TTG$_1$CTGACT-5' | 1678.61 |
| 77 | 5'-<u>U</u>CAGTCG$_1$TTAC-X-CATTG$_1$CTGAC<u>U</u>-5' | 1500.97 |
| 78 | 5'-TCAGTCG$_1$TTAoC-X-CoATTG$_1$CTGACT-5' | 927.15 |
| 79 | 5'-TAGToCG$_2$TTTTT-X-TTTTTG$_2$CoTGTAT-5' | 1013.11 |
| 80 | 5'-TCTGToCG$_2$TTGT-X-TGTTG$_2$CoTGTCT-5' | 1498.64 |
| 81 | 5'-TAGoToCG$_2$TTTTT-X-TTTTTG$_2$CoToGTAT-5' | 1019.68 |

TABLE VI(f)-continued

Human PBMC Assay for IL-12 (24 hours)

| Seq. ID. No./ Oligo No. | Sequences and Modification (5'-3') | IL-12 (pg/ml ± SD) at 10 µg/ml |
|---|---|---|
| 82 | 5'-TCG$_2$oToCG$_2$AoCG$_2$AT-X-TAG$_2$CoAG$_2$CoToG$_2$CT-5' | 1220.94 |
| 84 | 5'-TCAGToCG$_2$TTAC-S-CATTG$_2$CoTGACT-5' | 1450.24; 1604.88 |
| 85 & 96 | 5'-TCTGoToCG$_2$TAG-Z-GATTG$_2$CoToGTCT-5' | 879.09; 1498.64 |
| 88 | 5'-TCG$_1$CG$_1$TTTL-Z-LTTTG$_1$CTG$_1$CT-5' | 1463.20 |
| 90 | 5'-TCG$_1$TCG$_1$TTTL-X-LTTTG$_1$CTG$_1$CT-5' | 1417.50 |
| 92 | 5'-TCAGTCG$_1$TTAC-X-CATTG$_1$CTGACT-5' | 1602.41 |
| Media | | 54.36; 196.06; 511.18 |

TABLE VI(g)

Induction of IL-6 in human B cell cultures (24 hours)

| Seq. ID. No./ Oligo No. | Sequences and Modification (5'-3') | IL-6 (pg/ml ± SD) at 10 µg/ml |
|---|---|---|
| 60 | 5'-TCTGTCG$_1$TTCUo-X-oUCTTG$_1$CTGTCT-5' | 359 ± 7 |
| 61 | 5'-TCTGTCG$_1$TTCoUo-X-oUoCTTG$_1$CTGTCT-5' | 570 ± 37 |
| 62 | 5'-TCTGTCG$_2$TTCU-X-UCTTG$_2$CTGTCT-5' | 333 ± 3 |
| 63 | 5'-CTGTCG$_2$TTCUC-X-CUCTTG$_2$CTGTC-5' | 593 ± 8 |
| 64 | 5'-TCG$_1$AACG$_1$TTCG-X-GCTTG$_1$CAAG$_1$CT-5' | 503 ± 28 |
| 65 & 95 | 5'-TCG$_1$AACG$_1$TTCG$_1$-L-GACAG$_1$CTGTCT-5' | 481 ± 13 |
| Medium | | 91 ± 0 |

TABLE VI(h)

Induction of IL-10 in human B cell cultures (24 hours)

| Seq. ID. No./ Oligo No. | Sequences and Modification (5'-3') | IL-10 (pg/ml ± SD) at 10 µg/ml |
|---|---|---|
| 60 | 5'-TCTGTCG$_1$TTCUo-X-oUCTTG$_1$CTGTCT-5' | 188 ± 0 |
| 61 | 5'-TCTGTCG$_1$TTCoUo-X-oUoCTTG$_1$CTGTCT-5' | 286 ± 3 |
| 62 | 5'-TCTGTCG$_2$TTCU-X-UCTTG$_2$CTGTCT-5' | 223 ± 10 |
| 63 | 5'-CTGTCG$_2$TTCUC-X-CUCTTG$_2$CTGTC-5' | 201 ± 2 |
| 64 | 5'-TCG$_1$AACG$_1$TTCG-X-GCTTG$_1$CAAG$_1$CT-5' | 268 ± 0 |
| 65 & 95 | 5'-TCG$_1$AACG$_1$TTCG$_1$-L-GACAG$_1$CTGTCT-5' | 212 ± 1 |
| Medium | | 86 ± 5 |

Exemplar TLR9 agonists from Table I were tested for immune stimulatory activity in the human PBMC assay for IFN-γ, MIP-1α and MIP-β, as described in Example 3. The results shown in Table VII(a) and VII(b) below demonstrate that specific chemical modifications to 3'-3' linked oligonucleotides will alter their TLR9 mediated IFN-γ, MIP-1α, and/or MIP-β activation profile in human PBMCs. More generally, these data demonstrate that specific chemical modifications to 3'-3' linked oligonucleotides can be used to increase or decrease IFN-γ, MIP-1α, and MIP-β activation.

TABLE VII(a)

Human PBMC Assay for IFN-γ, MIP-1α and MIP-β

| Seq. ID. No./ Oligo No. | Sequences and Modification (5'-3') | IFN-γ (pg/ml) at 10 μg/ml | MIP-1α (pg/ml) at 10 μg/ml | MIP-β (pg/ml) at 10 μg/ml |
|---|---|---|---|---|
| 1 | 5'-TCAGTCG$_1$TTAC-X-CATTG$_1$CTGACT-5' | 86 | 28 | 1108 |
| 2 | 5'-TCTGTCG$_1$TTAG-X-GATTG$_1$CTGTCT-5' | 38.5 | 11 | 568.5 |
| 3 | 5'-CAGTCG$_1$TTCAG-X-GACTTG$_1$CTGAC-5' | 29 | 8.5 | 465.5 |
| 4 | 5'-TCTGTCG$_1$TTTT-X-TTTTG$_1$CTGTCT-5' | 31.5 | 14 | 648.5 |
| 5 | 5'-TCTGTCG$_1$TTGT-X-TGTTG$_1$CTGTCT-5' | 52.5 | 12 | 679 |
| 6 | 5'-TAGTCG$_1$TTTTT-X-TTTTTG$_1$CGTAT-5' | 66.5 | 15.5 | 799 |
| 7 | 5'-TGGTCG$_1$TTCTT-X-TTCTTG$_1$CTGGT-5' | 68.5 | 17 | 889.5 |
| 8 | 5'-TAGTCG$_1$TTGTA-X-ATGTTG$_1$CTGAT-5' | 77 | 20 | 1174 |
| 9 | 5'-TAGTCG$_1$TTCTC-X-CTCTTG$_1$CTGAT-5' | 93.5 | 26.5 | 1240.5 |
| 10 | 5'-TCG$_1$TCG$_1$TTCTT-X-TTCTTG$_1$CTG$_1$CT-5' | 59.5 | 29.5 | 1007 |
| 11 | 5'-TCG$_1$TACG$_1$TACG$_1$-X-G$_1$CATG$_1$CATG$_1$CT-5' | 5237.5 | 83 | 2931.5 |
| 12 | 5'-TCG$_1$TCG$_1$ACG$_1$AT-X-TAG$_1$CAG$_1$CTG$_1$CT-5' | 2199.7 | 24.7 | 2363 |
| 13 | 5'-TCG$_1$ATCG$_1$ATCG$_1$-X-G$_1$CTAG$_1$CTAG$_1$CT-5' | 5619.5 | 173 | 2479 |
| Media | | 40 | 6 | 187 |

TABLE VII(b)

Human PBMC Assay for IFN-γ, MIP-1α and MIP-β

| Seq. ID. No./ Oligo No. | Sequences and Modification (5'-3') | IFN-γ (pg/ml) at 10 μg/ml | MIP-1α (pg/ml) at 10 μg/ml | MIP-β (pg/ml) at 10 μg/ml |
|---|---|---|---|---|
| 24 | 5'-TCAGTCG$_2$TTAC-X-CATTG$_2$CTGACT-5' | 11.29 | 84.49 | 1373.07 |
| 25 | 5'-TCTGTCG$_2$TTAG-X-GATTG$_2$CTGTCT-5' | 14.44 | 90.61 | 1557.81 |
| 26 | 5'-CAGTCG$_2$TTCAG-X-GACTTG$_2$CTGAC-5' | 11.29 | 84.49 | 1337.00 |
| 27 | 5'-TCTGTCG$_2$TTTT-X-TTTTG$_2$CTGTCT-5' | 13.66 | 109.05 | 1746.19 |
| 28 | 5'-TCTGTCG$_2$TTGT-X-TGTTG$_2$CTGTCT-5' | 12.08 | 87.58 | 1337.01 |
| 29 | 5'-TAGTCG$_2$TTTTT-X-TTTTTG$_2$CGTAT-5' | 12.87 | 82.12 | 1428.54 |
| 30 | 5'-TGGTCG$_2$TTCTT-X-TTCTTG$_2$CTGGT-5' | 11.29 | 105.04 | 1839.64 |
| 31 | 5'-TAGTCG$_2$TTGTA-X-ATGTTG$_2$CTGAT-5' | 13.66 | 113.18 | 1995.04 |
| 32 | 5'-TAGTCG$_2$TTCTC-X-CTCTTG$_2$CTGAT-5' | 12.08 | 107.78 | 1603.54 |
| 33 | 5'-TCG$_2$TCG$_2$TTCTT-X-TTCTTG$_2$CTG$_2$CT-5' | 13.66 | 150.26 | 2785.79 |
| 34 | 5'-TCG$_2$TACG$_2$TACG$_2$-X-G$_2$CATG$_2$CATG$_2$CT-5' | 13.66 | 195.82 | 3966.88 |

TABLE VII(b)-continued

Human PBMC Assay for IFN-γ, MIP-1α and MIP-β

| Seq. ID. No./ Oligo No. | Sequences and Modification (5'-3') | IFN-γ (pg/ml) at 10 µg/ml | MIP-1α (pg/ml) at 10 µg/ml | MIP-β (pg/ml) at 10 µg/ml |
|---|---|---|---|---|
| 35 | 5'-TCG$_2$TCG$_2$ACG$_2$AT-X-TAG$_2$CAG$_2$CTG$_2$CT-5' | 10.50 | 134.83 | 2878.33 |
| 36 | 5'-TCG$_2$ATCG$_2$ATCG$_2$-X-G$_2$CTAG$_2$CTAG$_2$CT-5' | 8.11 | 107.78 | 2343.94 |
| media | | 3.25 | 6.11 | 149.2 |

Exemplar TLR9 agonists from Table I were tested for immune stimulatory activity in the human PBMC assay for MCP-1 and IFN-α, as described in Example 3. The results shown in Table VIII(a) and VIII(b) below demonstrate that specific chemical modifications to 3'-3' linked oligonucleotides will alter their TLR9 mediated MCP-1 and/or IFN-α activation profile in human PBMCs. More generally, these data demonstrate that specific chemical modifications to 3'-3' linked oligonucleotides can be used to increase or decrease MCP-1 and IFN-α activation.

TABLE VIII(a)

Human PBMC Assay for MCP-1 and IFN-α

| Seq. ID. No./ Oligo No. | Sequences and Modification (5'-3') | MCP-1 (pg/ml) at 10 µg/ml | IFN-α (pg/ml) at 10 µg/ml |
|---|---|---|---|
| 1 | 5'-TCAGTCG$_1$TTAC-X-CATTG$_1$CTGACT-5' | 3774.5 | 86 |
| 2 | 5'-TCTGTCG$_1$TTAG-X-GATTG$_1$CTGTCT-5' | 841 | 38.5 |
| 3 | 5'-CAGTCG$_1$TTCAG-X-GACTTG$_1$CTGAC-5' | 3503 | 29 |
| 4 | 5'-TCTGTCG$_1$TTTT-X-TTTTG$_1$CTGTCT-5' | 2514 | 31.5 |
| 5 | 5'-TCTGTCG$_1$TTGT-X-TGTTG$_1$CTGTCT-5' | 2134.5 | 52.5 |
| 6 | 5'-TAGTCG$_1$TTTTT-X-TTTTTG$_1$CGTAT-5' | 2154 | 66.5 |
| 7 | 5'-TGGTCG$_1$TTCTT-X-TTCTTG$_1$CTGGT-5' | 4201.5 | 68.5 |
| 8 | 5'-TAGTCG$_1$TTGTA-X-ATGTTG$_1$CTGAT-5' | 3620 | 77 |
| 9 | 5'-TAGTCG$_1$TTCTC-X-CTCTTG$_1$CTGAT-5' | 4885 | 935 |
| 10 | 5'-TCG$_1$TCG$_1$TTCTT-X-TTCTTG$_1$CTG$_1$CT-5' | 2672 | 59.5 |
| 11 | 5'-TCG$_1$TACG$_1$TACG$_1$-X-G$_1$CATG$_1$CATG$_1$CT-5' | 6793 | 5237.5 |
| 12 | 5'-TCG$_1$TCG$_1$ACG$_1$AT-X-TAG$_1$CAG$_1$CTG$_1$CT-5' | 6251 | 2199.7 |
| 13 | 5'-TCG$_1$ATCG$_1$ATCG$_1$-X-G$_1$CTAG$_1$CTAG$_1$CT-5' | 6686 | 5619.5 |
| Media | | 534 | 40 |

TABLE VIII(b)

Human PBMC Assay for MCP-1 and IFN-α

| Seq. ID. No./ Oligo No. | Sequences and Modification (5'-3') | MCP-1 (pg/ml) at 10 µg/ml | IFN-α (pg/ml) at 10 µg/ml |
|---|---|---|---|
| 24 | 5'-TCAGTCG$_2$TTAC-X-CATTG$_2$CTGACT-5' | 12480.44 | 62.03 |
| 25 | 5'-TCTGTCG$_2$TTAG-X-GATTG$_2$CTGTCT-5' | 50410.30 | 18.07 |
| 26 | 5'-CAGTCG$_2$TTCAG-X-GACTTG$_2$CTGAC-5' | 3982.45 | 42.09 |
| 27 | 5'-TCTGTCG$_2$TTTT-X-TTTTG$_2$CTGTCT-5' | 53685.37 | 13.28 |

TABLE VIII(b)-continued

Human PBMC Assay for MCP-1 and IFN-α

| Seq. ID. No./ Oligo No. | Sequences and Modification (5'-3') | MCP-1 (pg/ml) at 10 µg/ml | IFN-α (pg/ml) at 10 µg/ml |
|---|---|---|---|
| 28 | 5'-TCTGTCG$_2$TTGT-X-TGTTG$_2$CTGTCT-5' | 6116.14 | 46.03 |
| 29 | 5'-TAGTCG$_2$TTTTT-X-TTTTTG$_2$CGTAT-5' | 26435.31 | 38.08 |
| 30 | 5'-TGGTCG$_2$TTCTT-X-TTCTTG$_2$CTGGT-5' | 12012.62 | 30.38 |
| 31 | 5'-TAGTCG$_2$TTGTA-X-ATGTTG$_2$CTGAT-5' | 53166.41 | 26.16 |
| 32 | 5'-TAGTCG$_2$TTCTC-X-CTCTTG$_2$CTGAT-5' | 36199.26 | 67.03 |
| 33 | 5'-TCG$_2$TCG$_2$TTCTT-X-TTCTTG$_2$CTG$_2$CT-5' | 42397.84 | 31.4 |
| 34 | 5'-TCG$_2$TACG$_2$TACG$_2$-X-G$_2$CATG$_2$CATG$_2$CT-5' | 62106.60 | 83.69 |
| 35 | 5'-TCG$_2$TCG$_2$ACG$_2$AT-X-TAG$_2$CAG$_2$CTG$_2$CT-5' | 41760.82 | 29.94 |
| 36 | 5'-TCG$_2$ATCG$_2$ATCG$_2$-X-G$_2$CTAG$_2$CTAG$_2$CT-5' | 25530.72 | 942.37 |
| media | | 267.37 | 0 |

Exemplar TLR9 agonists from Table I were tested for immune stimulatory activity in the human PBMC and pDC assays for IFN-α, IL6, and IL-12, as described in Example 3. The results shown in Table IX(a), IX(b), IX(c), IX(d), IX(e), IX(f), and IX(g) below demonstrate that specific chemical modifications to 3'-3' linked oligonucleotides will alter their TLR9 mediated IFN-α activation profile in human PBMCs and pDCs. More generally, these data demonstrate that specific chemical modifications to 3'-3' linked oligonucleotides can be used to increase or decrease IFN-α, IL-6, and IL-12 activation.

TABLE IX(a)

Human PBMC Assay for IFN-α

| Seq. ID. No./ Oligo No. | Sequences and Modification (5'-3') | IFN-α (pg/ml) at 10 µg/ml |
|---|---|---|
| 10 | 5'-TCG$_1$TCG$_1$TTCTT-X-TTCTTG$_1$CTG$_1$CT-5' | 142.5 |
| 11 | 5'-TCG$_1$TACG$_1$TACG$_1$-X-G$_1$CATG$_1$CATG$_1$CT-5' | 8065.5 |
| 12 | 5'-TCG$_1$TCG$_1$ACG$_1$AT-X-TAG$_1$CAG$_1$CTG$_1$CT-5' | 7270.5 |
| 13 | 5'-TCG$_1$ATCG$_1$ATCG$_1$-X-G$_1$CTAG$_1$CTAG$_1$CT-5' | 8437 |
| Media | | 109.5 |

TABLE IX(b)

Human PBMC Assay for IFN-α (24 hours)[a]

| Seq. ID. No./ Oligo No. | Sequences and Modification (5'-3') | IFN-α (pg/ml ± SD) at 10 µg/ml |
|---|---|---|
| 60 | 5'-TCTGTCG$_1$TTC<u>U</u>o-X-o<u>U</u>CTTG$_1$CTGTCT-5' | 257.5 ± 539.4 |
| 61 | 5'-TCTGTCG$_1$TT<u>C</u>o<u>U</u>o-X-o<u>U</u>o<u>C</u>TTG$_1$CTGTCT-5' | 39.0 ± 88.5 |
| 62 | 5'-TCTGTCG$_2$TT<u>CU</u>-X-<u>UC</u>TTG$_2$CTGTCT-5' | 84.4 ± 143.2 |
| 63 | 5'-CTGTCG$_2$TTC<u>UC</u>-X-<u>CU</u>CTTG$_2$CTGTC-5' | 34.0 ± 37.1 |
| 64 | 5'-TCG$_1$AACG$_1$TT<u>CG</u>-X-<u>GC</u>TTG$_1$CAAG$_1$CT-5' | 1165 ± 704.7 |
| 65 & 95 | 5'-TCG$_1$AACG$_1$TTCG$_1$-L-<u>GA</u>CAG$_1$CTGTCT-5' | 2494.3 ± 1880.1 |
| Medium | | 22.2 ± 39.8 |

[a]Data are mean of 10 donors

TABLE IX(c)

Human PBMC Assay for IFN-α (24 hours)

| Seq. ID. No./ Oligo No. | Sequences and Modification (5'-3') | IFN-α (pg/ml) at 10 μg/ml |
|---|---|---|
| 68 | 5'-TCTGTCG$_2$TTCU-X-UCTTG$_2$CTGCTC-5' | 53.42 |
| 69 | 5'-CTGTCG$_2$TTCUC-X-CUCTTG$_2$CTGCTC-5' | 56.30 |
| 70 | 5'-TCG$_1$AACG$_1$TTCG-X-GCTTG$_1$CAAG$_1$CT-5' | 622.25 |
| 71 & 95 | 5'-TCG$_1$AACG$_1$TTCG$_1$-L-GACAG$_1$CTGTCT-5' | 1823.24 |
| 75 | 5'-TCAGTCG$_1$TTAC-X-CATTG$_1$CTGACT-5' | 97.42 |
| 77 | 5'-UCAGTCG$_1$TTAC-X-CATTG$_1$CTGACU-5' | 92.64 |
| 78 | 5'-TCAGTCG$_1$TTAoC-X-CoATTG$_1$CTGACT-5' | 86.38 |
| 79 | 5'-TAGToCG$_2$TTTTT-X-TTTTTG$_2$CoTGTAT-5' | 86.38 |
| 80 | 5'-TCTGToCG$_2$TTGT-X-TGTTG$_2$CoTGTCT-5' | 66.13 |
| 81 | 5'-TAGoToCG$_2$TTTTT-X-TTTTTG$_2$CoToGTAT-5' | 92.10 |
| 82 | 5'-TCG$_2$oToCG$_2$AoCG$_2$AT-X-TAG$_2$CoAG$_2$CoToG$_2$CT-5' | 65.86 |
| 84 | 5'-TCAGToCG$_2$TTAC-S-CATTG$_2$CoTGACT-5' | 86.38; 761.92 |
| 85 & 96 | 5'-TCTGoToCG$_2$TAG-Z-GATTG$_2$CoToGTCT-5' | 98.37; 592.17 |
| 88 | 5'-TCG$_1$CG$_1$TTTL-Z-LTTTG$_1$CTG$_1$CT-5' | 958.92 |
| 90 | 5'-TCG$_1$TCG$_1$TTTL-X-LTTTG$_1$CTG$_1$CT-5' | 710.90 |
| 92 | 5'-TCAGTCG$_1$TTAC-X-CATTG$_1$CTGACT-5' | 92.64 |
| Media | | 32.9; 64.8; 14.5 |

TABLE IX(d)

Human pDC Assay for IFN-α (24 hours)[a]

| Seq. ID. No./ Oligo No. | Sequences and Modification (5'-3') | IFN-α (pg/ml ± SD) at 10 μg/ml |
|---|---|---|
| 60 | 5'-TCTGTCG$_1$TTCUo-X-oUCTTG$_1$CTGTCT-5' | 1509.5 ± 2612.7 |
| 61 | 5'-TCTGTCG$_1$TTCUo-X-oUoCTTG$_1$CTGTCT-5' | 1598.9 ± 3727.2 |
| 62 | 5'-TCTGTCG$_2$TTCU-X-UCTTG$_2$CTGTCT-5' | 3415.6 ± 3903.6 |
| 63 | 5'-CTGTCG$_2$TTCUC-X-CUCTTG$_2$CTGTC-5' | 2180.1 ± 3882.0 |
| 64 | 5'-TCG$_1$AACG$_1$TTCG-X-GCTTG$_1$CAAG$_1$CT-5' | 32956.8 ± 2639.9 |
| 65 & 95 | 5'-TCG$_1$AACG$_1$TTCG$_1$-L-GACAG$_1$CTGTCT-5' | 47746.2 ± 53192.1 |
| Medium | | 106.6 ± 156.5 |

[a]Data are mean of 10 donors

TABLE IX(e)

Human pDC Assay for IFN-α (24 hours)

| Seq. ID. No./ Oligo No. | Sequences and Modification (5'-3') | IFN-α (pg/ml ± SD) at 10 µg/ml |
|---|---|---|
| 67 | 5'-TCTGTCG$_1$TTCUo-X-oUoCTTG$_1$CTGCTC-5' | 174.81 |
| 68 | 5'-TCTGTCG$_2$TTCU-X-UCTTG$_2$CTGCTC-5' | 900.94 |
| 69 | 5'-CTGTCG$_2$TTCUC-X-CUCTTG$_2$CTGCTC-5' | 475.64 |
| 70 | 5'-TCG$_1$AACG$_1$TTCG-X-GCTTG$_1$CAAG$_1$CT-5' | 4813.76 |
| 71 & 95 | 5'-TCG$_1$AACG$_1$TTCG$_1$-L-GACAG$_1$CTGTCT-5' | 15494.15 |
| 72 | 5'-TCTGTCG$_1$TTAG-S-GATTG$_1$CTGTCT-5' | 1934.09 |
| 73 | 5'-CAGTCG$_1$TTCAG-Z-GACTTG$_1$CTGAC-5' | 2978.9 |
| 74 | 5'-TCG$_1$TCG$_1$ACG$_1$AT-S-TAG$_1$CAG$_1$CTG$_1$CT-5' | 57697.2 |
| 75 | 5'-TCAGTCG$_1$TTAC-X-CATTG$_1$CTGACT-5' | 8171 |
| 77 | 5'-UCAGTCG$_1$TTAC-X-CATTG$_1$CTGACU-5' | 598.6 |
| 78 | 5'-TCAGTCG$_1$TTAoC-X-CoATTG$_1$CTGACT-5' | 4245.4 |
| 79 | 5'-TAGToCG$_2$TTTTT-X-TTTTTG$_2$CoTGTAT-5' | 2807.2 |
| 80 | 5'-TCTGToCG$_2$TTGT-X-TGTTG$_2$CoTGTCT-5' | 6133.96 |
| 81 | 5'-TAGoToCG$_2$TTTTT-X-TTTTTG$_2$CoToGTAT-5' | 1028.1 |
| 82 | 5'-TCG$_2$oToCG$_2$AoCG$_2$AT-X-TAG$_2$CoAG$_2$CoToG$_2$CT-5' | 17873.5 |
| 84 | 5'-TCAGToCG$_2$TTAC-S-CATTG$_2$CoTGACT-5' | 190.42.1 |
| 85 & 96 | 5'-TCTGoToCG$_2$TAG-Z-GATTG$_2$CoToGTCT-5' | 11673.4 |
| 86 | 5'-TCG$_1$TCG$_1$TTTL-S-LTTTG$_1$CTG$_1$CT-5' | 10408.2 |
| 88 | 5'-TCG$_1$CG$_1$TTTL-Z-LTTTG$_1$CTG$_1$CT-5' | 14783.3 |
| 89 | 5'-LTCG$_1$TCG$_1$TTTL-Z-LTTTG$_1$CTG$_1$CTL-5' | 6819.14 |
| 90 | 5'-TCG$_1$TCG$_1$TTTL-X-LTTTG$_1$CTG$_1$CT-5' | 14515.1 |
| 92 | 5'-TCAGTCG$_1$TTAC-X-CATTG$_1$CTGACT-5' | 307.8 |
| Media | | 32.9; 0; 0.105 |

TABLE IX(f)

Human pDC Assay for IL-6 (24 hours)

| Seq. ID. No./ Oligo No. | Sequences and Modification (5'-3') | IL-6 (pg/ml) 10 µg/ml |
|---|---|---|
| 66 | 5'-TCTGTCG$_1$TTCUo-X-oUCTTG$_1$CTGCTC-5' | 2384.36 |
| 67 | 5'-TCTGTCG$_1$TTCUo-X-oUoCTTG$_1$CTGCTC-5' | 1405.14 |
| 68 | 5'-TCTGTCG$_2$TTCU-X-UCTTG$_2$CTGCTC-5' | 2851.75 |
| 69 | 5'-CTGTCG$_2$TTCUC-X-CUCTTG$_2$CTGCTC-5' | 1598.06 |
| 70 | 5'-TCG$_1$AACG$_1$TTCG-X-GCTTG$_1$CAAG$_1$CT-5' | 1625.8 |
| 71 & 95 | 5'-TCG$_1$AACG$_1$TTCG$_1$-L-GACAG$_1$CTGTCT-5' | 1648.17 |
| 80 | 5'-TCTGToCG$_2$TTGT-X-TGTTG$_2$CoTGTCT-5' | 13805.44 |

TABLE IX(f)-continued

Human pDC Assay for IL-6 (24 hours)

| Seq. ID. No./ Oligo No. | Sequences and Modification (5'-3') | IL-6 (pg/ml) 10 µg/ml |
|---|---|---|
| 84 | 5'-TCAGToCG$_2$TTAC-S-CATTG$_2$CoTGACT-5' | 19405.66 |
| 85 & 96 | 5'-TCTGoToCG$_2$TAG-Z-GATTG$_2$CoToGTCT-5' | 17253.59 |
| 88 | 5'-TCG$_1$CG$_1$TTTL-Z-LTTTG$_1$CTG$_1$CT-5' | 9277.99 |
| 90 | 5'-TCG$_1$TCG$_1$TTTL-X-LTTTG$_1$CTG$_1$CT-5' | 5092.34 |
| Media | | 1847.09; 1918.47 |

TABLE IX(g)

Human pDC Assay for IL-12 (24 hours)

| Seq. ID. No./ Oligo No. | Sequences and Modification (5'-3') | IL-12 (pg/ml) 10 µg/ml |
|---|---|---|
| 66 | 5'-TCTGTCG$_1$TTC<u>U</u>o-X-o<u>U</u>CTTG$_1$CTGCTC-5' | 624.29 |
| 67 | 5'-TCTGTCG$_1$TT<u>C</u>o<u>U</u>o-X-o<u>U</u>o<u>C</u>TTG$_1$CTGCTC-5' | 492.13 |
| 68 | 5'-TCTGTCG$_2$TT<u>CU</u>-X-<u>UC</u>TTG$_2$CTGCTC-5' | 724.53 |
| 69 | 5'-CTGTCG$_2$TTC<u>UC</u>-X-<u>UC</u>CTTG$_2$CTGCTC-5' | 895.07 |
| 70 | 5'-TCG$_1$AACG$_1$TT<u>CG</u>-X-<u>GC</u>TTG$_1$CAAG$_1$CT-5' | 369.77 |
| 71 & 95 | 5'-TCG$_1$AACG$_1$TTCG$_1$-L-<u>GA</u>CAG$_1$CTGTCT-5' | 567.95 |
| 80 | 5'-TCTGToCG$_2$TTGT-X-TGTTG$_2$CoTGTCT-5' | 1498.64 |
| 84 | 5'-TCAGToCG$_2$TTAC-S-CATTG$_2$CoTGACT-5' | 1604.88 |
| 85 & 96 | 5'-TCTGoToCG$_2$TAG-Z-GATTG$_2$CoToGTCT-5' | 1498.64 |
| 88 | 5'-TCG$_1$CG$_1$TTTL-Z-LTTTG$_1$CTG$_1$CT-5' | 1463.20 |
| 90 | 5'-TCG$_1$TCG$_1$TTTL-X-LTTTG$_1$CTG$_1$CT-5' | 1417.50 |
| Media | | 349.26; 397.1 |

Exemplar TLR9 agonists from Table I were tested for their induction of IL-12 and IL-6 in mouse spleen cell cultures, as described in Example 3. The results shown in Table X(a) and X(b) below demonstrate that specific chemical modifications to 3'-3' linked oligonucleotides will alter their TLR9 mediated IL-6 and/or IL-12 activation profile in spleen cells and that this activation profile may be dose dependent depending on the chemical modification. More generally, these data demonstrate that specific chemical modifications to 3'-3' linked oligonucleotides can be used to increase or decrease IL-6 and IL-12 activation.

TABLE X(a)

Induction of IL-12 and IL-6 Secretion in Mouse Spleen Cell Cultures

| Seq. ID. No./ Oligo No. | Sequence | IL-6 (pg/ml ± SD) at 1 µg/ml | at 3 µg/ml | IL-12 (pg/ml ± SD) at 1 µg/ml | at 3 µg/ml |
|---|---|---|---|---|---|
| 38 | 5'-TCTGACG$_1$TTCT-Y-TCTTG$_1$CAGTCT-5' | 8354 ± 32 | 24508 ± 86 | 909 ± 17 | 876 ± 89 |
| 39 | 5'-TCG$_1$AACG$_1$TTCG$_1$-Y-G$_1$CTTG$_1$CAAG$_1$CT-5' | 3371 ± 102 | 15012 ± 25 | 621 ± 12 | 517 ± 19 |
| 40 | 5'-TCG$_1$TCG$_1$TTCTG-Y-GTCTTG$_1$CTG$_1$CT-5' | 361 ± 4 | 4072 ± 1 | 451 ± 13 | 279 ± 0 |

TABLE X(a)-continued

Induction of IL-12 and IL-6 Secretion in Mouse Spleen Cell Cultures

| Seq. ID. No./ Oligo No. | Sequence | IL-6 (pg/ml ± SD) at 1 µg/ml | IL-6 (pg/ml ± SD) at 3 µg/ml | IL-12 (pg/ml ± SD) at 1 µg/ml | IL-12 (pg/ml ± SD) at 3 µg/ml |
|---|---|---|---|---|---|
| 41 | 5'-TCAGTCGTTAG-Y-GATTGCTGACT-5' | 2496 ± 69 | 17796 ± 3 | 856 ± 12 | 626 ± 6 |
| 42 | 5'-TCTGTCGTTCT-Y-TCTTGCTGTCT-5' | 8034 ± 95 | 22124 ± 57 | 659 ± 7 | 455 ± 18 |
| 43 | 5'-TCGTTGL-Y-LGTTGCT-5' | 3127 ± 22 | 14412 ± 32 | 532 ± 11 | 536 ± 27 |
| 47 & 93 | 5'-TCG$_1$AACG$_1$TTCG$_1$-M-TCTTG$_1$CTGTCT-5' | 2685 ± 29 | 15663 ± 35 | 957 ± 2 | 566 ± 18 |
| 48 & 94 | 5'-TCG$_1$AACG$_1$TTCG$_1$-M-GACAG$_1$CTGTCT-5' | 3199 ± 69 | 17016 ± 11 | 792 ± 3 | 528 ± 2 |
| PBS | | 0.00 | 0.00 | 87 ± 16 | 87 ± 16 |

TABLE X(b)

Induction of IL-12 and IL-6 Secretion in Mouse Spleen Cell Cultures

| Seq. ID. No./ Oligo No. | Sequences and Modification (5'-3') | IL-12 (pg/ml ± SD) at 1 µg/ml | IL-6 (pg/ml ± SD) at 1 µg/ml |
|---|---|---|---|
| 60 | 5'-TCTGTCG$_1$TTCUo-X-oUCTTG$_1$CTGTCT-5' | 4066 ± 47 | 78 ± 14 |
| 61 | 5'-TCTGTCG$_1$TTCoUo-X-oUoCTTG$_1$CTGTCT-5' | 2438 ± 81 | 164 ± 21 |
| 62 | 5'-TCTGTCG$_2$TTCU-X-UCTTG$_2$CTGTCT-5' | 1782 ± 67 | 120 ± 36 |
| 63 | 5'-CTGTCG$_2$TTCUC-X-CUCTTG$_2$CTGTC-5' | 2496 ± 105 | 215 ± 19 |
| 64 | 5'-TCG$_1$AACG$_1$TTCG-X-GCTTG$_1$CAAG$_1$CT-5' | 64796 ± 60 | 3776 ± 25 |
| 65 & 95 | 5'-TCG$_1$AACG$_1$TTCG$_1$-L-GACAG$_1$CTGTCT-5' | 8245 ± 244 | 3776 ± 46 |
| Medium | | 921 ± 60 | 38 ± 0 |

Exemplar TLR9 agonists from Table I were tested for their induction of IL-1Ra, IL-6 and IL-112p40p70 in human PBMC cultures, as described in Example 3. The results shown in Table XI below demonstrate that specific chemical modifications to 3'-3' linked oligonucleotides will alter their TLR9 mediated IL-1Rα, IL-6, and IL-12p40p70 activation profile in human PBMCs. More generally, these data demonstrate that specific chemical modifications to 3'-3' linked oligonucleotides can be used to increase or decrease IL-1Rα, IL-6, and IL-12p40p70 activation.

TABLE XI

IL-1Rα, IL-6 and IL-12p40p70 in human PBMC

| Seq. ID. No./ Oligo No | Sequence | IL-1Rα | IL-6 | IL-12p40p70 |
|---|---|---|---|---|
| 43 | 5'-TCGTTGL-Y-LGTTGCT-5' | 1595.5 | 1079.5 | 160.5 |
| 44 | 5'-TCGTTGM-Y-MGTTGCT-5' | 1775.0 | 931.5 | 148.0 |
| 45 | 5'-TCG$_1$TTGM-Y-MGTTG$_1$CT-5' | 954.0 | 1235.5 | 71.0 |
| 46 | 5'-TCGTTGM-X-MGTTGCT-5' | 1550.0 | 800.0 | 127.0 |
| PBS | | 187.0 | 36.0 | 21.0 |

As described above, the invention provides, in a first aspect, oligonucleotide-based synthetic agonists of TLR9. Based upon certain chemical modifications to the base, sugar, linkage, or linker, the agonists of TLR9 may possess increased stability when associated, duplexed, with other of the TLR9 agonist molecules, while retaining an accessible 5'-end.

In a second aspect, the invention provides a composition comprising an oligonucleotide-based TLR9 agonist ("a compound") according to the invention and a physiologically acceptable carrier. The term "physiologically acceptable" generally refers to a material that does not interfere with the effectiveness of the compound and that is compatible with a biological system such as a cell, cell culture, tissue, or organism.

As used herein, the term "carrier" encompasses any excipient, diluent, filler, salt, buffer, stabilizer, solubilizer, oil, lipid, lipid containing vesicle, microspheres, liposomal encapsulation, or other material well known in the art for use in physiologically acceptable formulations. It will be understood that the characteristics of the carrier, excipient, or diluent will depend on the route of administration for a particular application. The preparation of physiologically acceptable formulations containing these materials is described in, e.g., *Remington's Pharmaceutical Sciences,* 18th Edition, ed. A. Gennaro, Mack Publishing Co., Easton, Pa., 1990.

The active compound is included in the physiologically acceptable carrier or diluent in an amount sufficient to deliver to a patient a prophylactically or therapeutically effective amount without causing serious toxic effects in the patient treated. The term an "effective amount" or a "sufficient amount" generally refers to an amount sufficient to affect a desired biological effect, such as beneficial results. Thus, an "effective amount" or "sufficient amount" will depend upon the context in which it is being administered. The effective dosage range of the physiologically acceptable derivatives can be calculated based on the weight of the parent compound to be delivered. If the derivative exhibits activity in itself, the effective dosage can be estimated as above using the weight of the derivative, or by other means known to those skilled in the art.

In a third aspect, the invention provides a vaccine. Vaccines according to this aspect comprise a composition according to the invention, and further comprise an antigen. An antigen is a molecule that elicits a specific immune response. Such antigens include, without limitation, proteins, peptides, nucleic acids, carbohydrates and complexes or combinations of any of the same. Antigens may be natural or synthetic and generally induce an immune response that is specific for that antigen. Any such antigen may optionally be linked to an immunogenic protein, such as keyhole limpet hemocyanin (KLH), cholera toxin B subunit, or any other immunogenic carrier protein.

Vaccines according to the invention may further include any of the plethora of known adjuvants, including, without limitation, Freund's complete adjuvant, KLH, monophosphoryl lipid A (MPL), alum, and saponins, including QS-21, imiquimod, R848, or combinations thereof.

In a fourth aspect, the invention provides methods for generating a TLR9-mediated immune response in a vertebrate, such methods comprising administering to the vertebrate a compound, composition or vaccine according to the invention. In some embodiments, the vertebrate is a mammal. For purposes of this invention, the term "mammal" is expressly intended to include humans and animals. In preferred embodiments, the compound, composition or vaccine is administered to a vertebrate in need of immune stimulation.

In the methods according to this aspect of the invention, administration of a compound, composition or vaccine according to the invention can be by any suitable route, including, without limitation, parenteral, oral, intratumoral, sublingual, transdermal, topical, intranasal, aerosol, intraocular, intratracheal, intrarectal, mucosal, vaginal, by gene gun, dermal patch or in eye drop or mouthwash form. Administration of the compound, composition or vaccine can be carried out using known procedures at dosages and for periods of time effective to reduce symptoms or surrogate markers of the disease. When administered systemically, the compound, composition or vaccine is preferably administered at a sufficient dosage to attain a blood level of a compound according to the invention from about 0.0001 micromolar to about 10 micromolar. For localized administration, much lower concentrations than this may be effective, and much higher concentrations may be tolerated without serious toxic effects. Preferably, a total dosage of a compound according to the invention ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

In certain preferred embodiments, a compound, composition or vaccine according to the invention is administered in combination with another agent, including without limitation antibodies, cytotoxic agents, allergens, antibiotics, antisense oligonucleotides, SiRNA, aptamers, ribozymes, targeted therapies, peptides, proteins, gene therapy vectors, DNA vaccines, and/or adjuvants to enhance the specificity or magnitude of the immune response.

For purposes of this aspect of the invention, the term "in combination with" means in the course of treating a disease or disorder in a patient, administering the compound, composition or vaccine according to the invention and/or the other agent in any order, including simultaneous administration, as well as temporally spaced order of up to several hours, days or weeks apart. Such combination treatment may also include more than a single administration of the compound, composition or vaccine according to the invention, and/or the other agent. The administration of the compound, composition or vaccine according to the invention and/or the other agent may be by the same or different routes.

The methods according to this aspect of the invention are useful for the prophylactic or therapeutic treatment of human or animal disease. For example, the methods are useful for pediatric and veterinary vaccine applications. The methods are also useful for model studies of the immune system.

In a fifth aspect, the invention provides methods for therapeutically treating a patient having a disease or disorder, such methods comprising administering to the patient a compound, composition or vaccine according to the invention. In various embodiments, the disease or disorder to be treated is cancer, an autoimmune disorder, infectious disease, airway inflammation, inflammatory disorders, allergy, asthma or a disease caused by a pathogen or allergen. Pathogens include for example bacteria, parasites, fungi, viruses, viroids, and prions. Administration is carried out as described for the fourth aspect of the invention.

The term "treatment" generally refers to an approach intended to obtain a beneficial or desired results, which may include alleviation of symptoms, or delaying or ameliorating a disease progression.

For purposes of the invention, the term "allergy" generally refers to an inappropriate immune response characterized by inflammation and includes, without limitation, food allergies and respiratory allergies. The term "airway inflammation" includes, without limitation, asthma. As used herein, the term "autoimmune disorder" refers to disorders in which "self" components (e.g., proteins) undergo attack by the immune system. Such includes autoimmune asthma. The term "cancer" includes, without limitation, any malignant growth or tumor caused by abnormal or uncontrolled cell proliferation and/or division. Cancers may occur in humans and/or animals and may arise in any and all tissues. Treating a patient having cancer with the invention may include administration of a compound, composition or vaccine according to the invention such that the abnormal or uncontrolled cell proliferation and/or division is affected.

In a sixth aspect, the invention provides methods for preventing a disease or disorder, such methods comprising administering to the patient a compound, composition or vaccine according to the invention. In various embodiments, the disease or disorder to be prevented is cancer, an autoimmune disorder, airway inflammation, inflammatory disorders, infectious disease, allergy, asthma or a disease caused by a pathogen. Pathogens include, without limitation, bacteria, parasites, fungi, viruses, viroids, and prions. Administration is carried out as described for the fourth aspect of the invention.

In any of the methods according to the invention, the compound, composition or vaccine according to the invention can be administered in combination with any other agent useful for preventing or treating the disease or condition that does not diminish the immune stimulatory effect of the compound, composition or vaccine according to the invention. In any of the methods according to the invention, the agent useful for preventing or treating the disease or condition includes, but is not limited to, vaccines, antigens, antibodies, cytotoxic agents, allergens, antibiotics, antisense oligonucleotides, TLR agonist, peptides, proteins, gene therapy vectors, DNA vaccines and/or adjuvants to enhance the specificity or magnitude of the immune response, or co-stimulatory molecules such as cytokines, chemokines, protein ligands, trans-activating factors, peptides and peptides comprising modified amino acids. For example, in the prevention and/or treatment of cancer, it is contemplated that the compound, composition or vaccine according to the invention may be administered in combination with a chemotherapeutic compound or a monoclonal antibody. Alternatively, the agent can include DNA vectors encoding for antigen or allergen. In these embodiments, the compound, composition or vaccine according to the invention can variously act as adjuvants and/or produce direct immunomodulatory effects.

The following examples are intended to further illustrate certain preferred embodiments of the invention and are not intended to limit the scope of the invention in any way.

EXAMPLE 1

Synthesis of Oligonucleotides, Pentane-1,3,5-triol, Pentane-1,5-diol and cis-1,3,5-Cyclohexanetriol Linkers and Functionalization of CPG and OligoPrep Solid Supports Control pore glass-derivatized 3-methyl-1,3,5-pentanetriol linker (5) was achieved from commercially available 3-methyl-1,3,5-triol 1 as shown in Scheme 1. Initially, bis-DMT protected alcohol 2 was prepared in good yield from 1 by treating with DMTCl in the presence of DMAP. The conventional method of derivatization of CPG was not possible due to the low yields of the succinylation product at 3-hydroxyl of 2, possibly due to steric effects. However, the linker derivatized CPG 5 was prepared by following the alternate approach which eliminates the need for making succinate 3 (Scheme 1). In this route, initially, the CPG beads were activated by treating with 3% trichloroacetic acid (TCA) in dichloromethane (DCM) at room temperature (r.t.) to liberate maximum number of reactive amino groups on the surface of CPG. The activated CPG beads were then derivatized with succinic anhydride in the presence of DMAP to provide CPG beads 4. Finally, CPG derivatized linker 5 was obtained by condensation of 2 with carboxylic groups of CPG 4 in the presence of N-(3-dimethylaminopropyl)-N'-ethylcarbodiimide hydrochloride (DEC)/DMAP. After derivatization, the residual carboxylic groups were eliminated by capping reaction with pentachlorophenol.

Scheme 1.
Synthesis of 3-methyl-1,3,5-pentanetriol linker and derivatization of CPG.

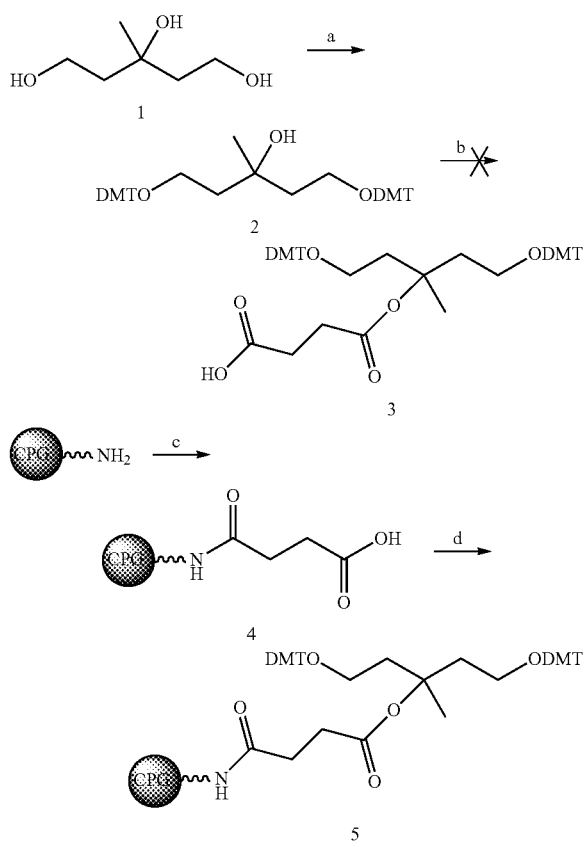

Reagents and conditions:
a DMTCl, DMAP, pyridine, 0° C.-r.t.;
b succinic anhydride, DMAP, pyridine;
c (i) 3% TCA in DCM; (ii) succinic anhydride, DMAP, pyridine;
d (i) 2, DMAP, TEA, DEC, pyridine; (ii) pentachlorophenol.

1,3,5-Pentanetriol linker derivatized CPG 10 and OligoPrep 11 were prepared starting from the commercially available diethyl 3-hydroxy glutarate 6 (Scheme 2). Reduction of 6 with LiAlH₄ yielded 1,3,5-pentanetriol 7 in quantitative yield. The triol 7 was then selectively protected with DMTCl in the presence of DMAP to afford bis-DMT protected alcohol 8, which was then successfully converted into succinate 9, which is ready to load on to the solid support, by treating with succinic anhydride in the presence of DMAP. Attachment of 9 to CPG was accomplished in quantitative loading yield in the presence of DIC/DMAP in pyridine/acetonitrile mixture (10). Whereas, the above protocol gave very poor loading yield in the case of OligoPrep250, a PVA solid support, functionalization. However, quantitative loading yield was achieved in the presence of TBTU/DMAP in acetonitrile (11). The loading was maintained at about ~40 μmol/g on CPG (10) and ~125 μmol/g on OligoPrep250 (11) supports, respectively, which increases the nucleotide coupling efficiencies and final yields.

Scheme 3.
Synthesis of pentanediol phosphoramididite.

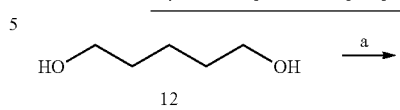

Scheme 2.
Synthesis of 1,3,5-pentanetriol linker and derivatization of CPG and OligoPrep solid supports.

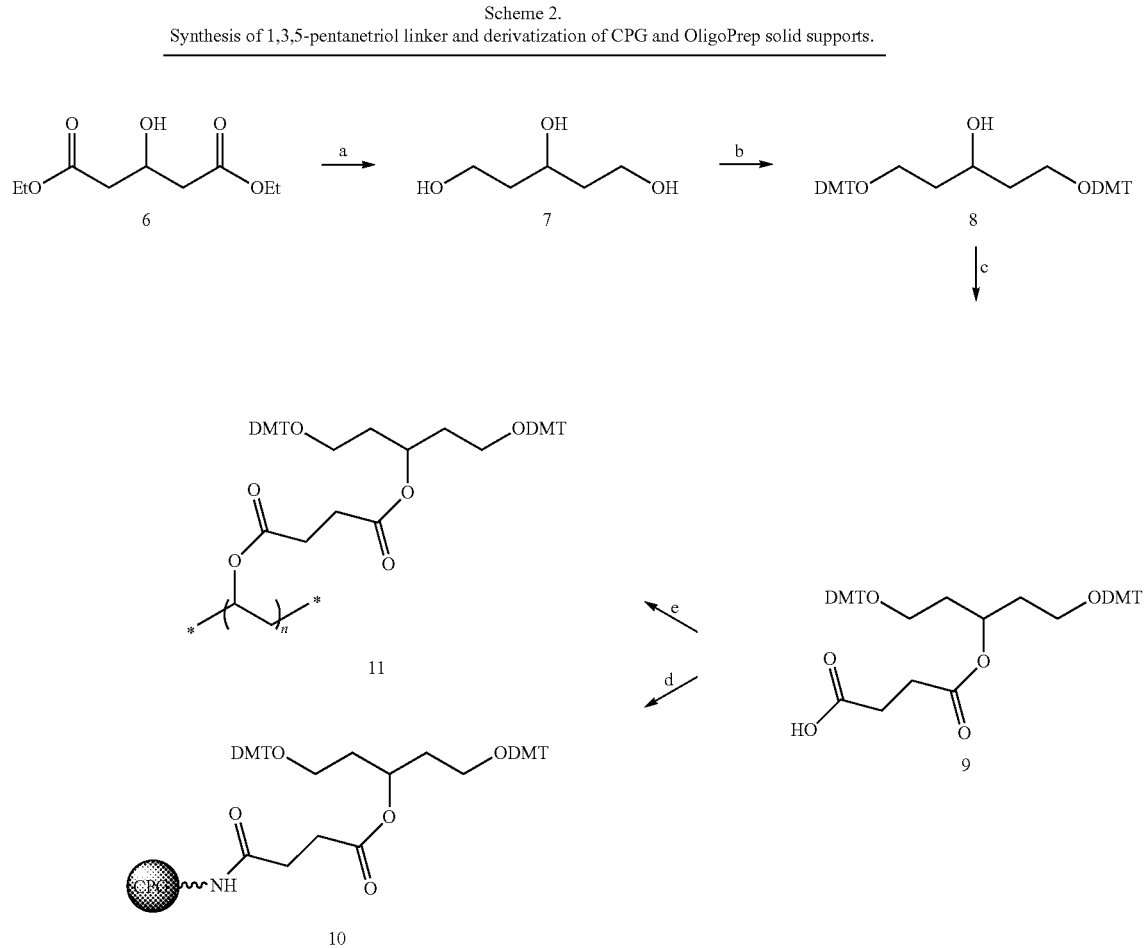

Reagents and conditions:
a  LiAlH4, THF, 0° C.-r.t.;
b  DMTCl, DMAP, pyridine, 0° C.-r.t.;
c  succinic anhydride, DMAP, pyridine;
d  LCAA-CPG, DMAP, DIC, pyridine, acetonitrile;
e  OligoPrep250, DMAP, TBTU, acetonitrile.

The C5 linker functionalized supports 10 and 11 are ideal for making immunomers with identical sequences. Immunomers with unidentical sequences also exhibited potent immune stimulatory activity in our studies. Appropriately protected C5 linker, such as 14 (Scheme 3), is required in order to make immunomers with unidentical sequences. One of the hydroxyl groups of commercially available 1,5-pentanediol was selectively protected with DMT followed by phosphitylation with 2-cyanoethyl N,N-diisopropylchlorophos-phosphoramidite afforded the required C5 linker 14 (Scheme 3).

-continued

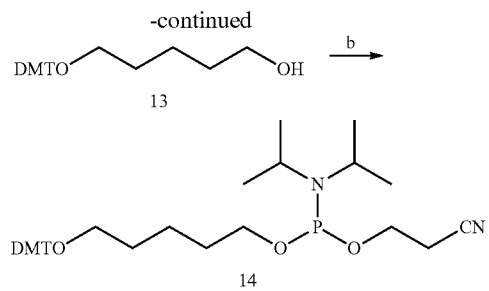

-continued

Reagents and conditions:
a DMTCl, DMAP, pyridine, -10° C.-r.t.;
b DIPEA, 2-cyanoethyl N,N-diisopropylchloro-phosphosphoramidite, NMI, DCM, 0° C.-r.t.

We have also focused our attention on the design and development of CpG DNA dendrimers as potent synthetic immune modulatory motifs. In order to make CpG DNA dendrimers, appropriately protected linker phosphoramidites are essential. The C5 linker phosphramidites 15 and 16 were prepared from di-DMT alcohols 2 and 8, respectively, by phosphitylation with 2-cyanoethyl N,N-diisopropylchloro-phosphosphoramidite as shown in Scheme 4.

Scheme 4.
Synthesis of pentanetriol phoshoramidites.

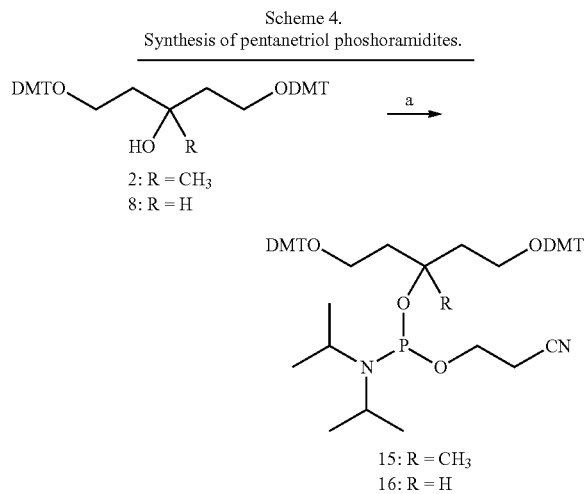

2: R = CH₃
8: R = H

15: R = CH₃
16: R = H

Reagents and conditions:
a DIPEA, 2-cyanoethyl N,N-diisopropylchlorophosphosphoramidite, NMI, DCM, 0° C.-r.t.

cis-Cyclohexanetriol linker derivatized with CPG 20 was accomplished as shown in Scheme 5. bis-DMT protected cis-1,3,5-cyclohexanetriol 18 was achieved from commercially available cis-1,3,5-cyclohexanetriol (17). The subsequent succinylation of the unprotected hydroxyl of 18 with succinic anhydride in the presence of DMAP afforded desired bis-DMT succinate 19 in 78% yield. Derivatization of CPG with succinate 19 was accomplished in quantitative loading yield (20, 40 μmol/g) in the presence of DIC/DMAP in pyridine/acetonitrile mixture.

Scheme 5.
Synthesis of cis-cyclohexane-1,3,5-triol linker and derivatization of CPG solid support.

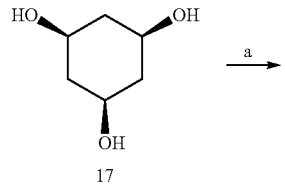

17

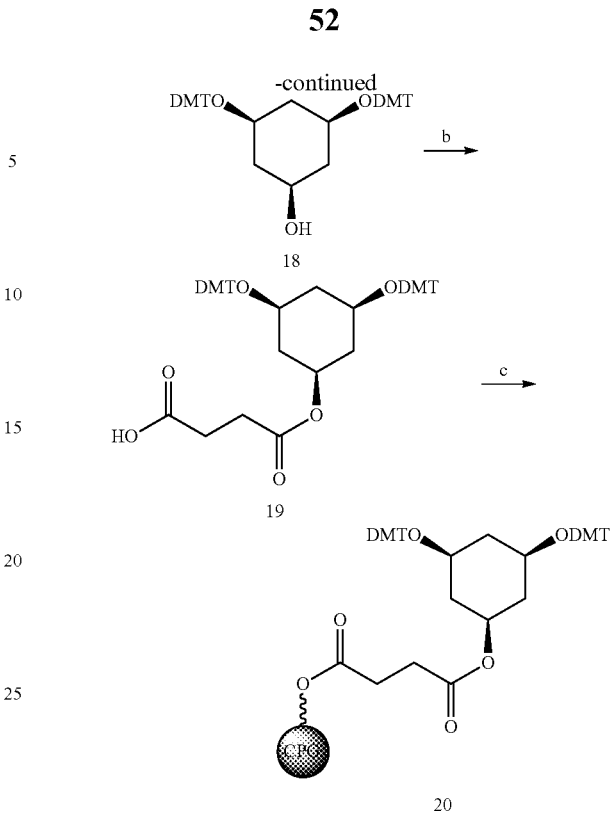

Reagents and conditions:
a DMTCl, DMAP, pyridine, 0° C.-r.t.;
b succinic anhydride, DMAP, pyridine, r.t.;
c LCAA-CPG, DMAP, DIC, pyridine, acetonitrile.

Reagents such as diethyl 3-hydroxy glutarate, lithium aluminum hydride (LiAlH₄), 4,4-dimethoxytrityl chloride (DMTCl), 4-dimethylaminopyridine (DMAP), succinic anhydride, O-(benzotriazol-1-yl)-N,N,N',N'-tetramethyluronium tetrafluoroborate (TBTU), N,N'-diisopropylcarbodiimide (DIC), N-(3-dimethylaminopropyl)-N'-ethylcarbodiimide hydrochloride (DEC), trichloroacetic acid (TCA), N-methylimidazole (NMI), triethylamine (TEA), diisopropylethylamine (DIPEA) and solvents such as pyridine, dichloromethane (DCM) and tetrahydrofuran (THF) were obtained from Sigma-Aldrich (St. Louis, Mo.) and used without further purification unless mentioned otherwise. Long chain alkyl amine controlled pore glass (CPG; 120-200 mesh, 500 Å, 90-120 μmol/g NH₂ groups) was obtained from CPG Inc. (Lincoln Park, N.J.) and OligoPrep250 was obtained from Merck KGaA (Germany). Cap A (acetic anhydride/2,6-lutidine/THF 1:1:8) and Cap B (N-methylimidazole/THF 16:84) reagents were obtained from Applied Biosystems (Foster City, Calif.). All reactions were performed in glassware which had been oven dried at 120° C. for at least 3 hrs prior to use. TLCs were run on silica gel 60 $F_{254}$ coated on aluminum sheets, and visualized by UV light or by a 5% phosphomolybdic acid (PMA) solution from Sigma-Aldrich (St. Louis, Mo.). Solvents such as ethyl acetate (EtOAc), hexanes, DCM, methanol, t-butyl methyl ether for chromatography were obtained from J. T. Baker and used without purification. Flash column chromatography was performed using silica gel 60 (mesh size 0.040-0.063 mm & 230-400 mesh ASTM) which was obtained from EMD Chemicals (Gibbstown, N.J.). NMR spectra were performed on Varian 400 MHz Unity Inova instrument. Chemical shifts (δ) are in ppm relative to TMS and all coupling constants (J) are in Hz.

1,5-Bis-dimethoxytrityloxy-3-methyl-pentan-3-ol (2). DMTCl (3.6 g, 10.5 mmol, 2.1 equiv) in pyridine (25 mL) was added drop wise to an ice cold (0° C.) and stirring solution of 3-methyl-1,3,5-pentanetiol (1, 0.7 g, 5 mmol) and DMAP (0.24 g) in dry pyridine (25 mL) under nitrogen atmosphere. The reaction mixture was allowed to slowly reach room temperature (~4 h) and continued stirring for overnight. TLC (hexanes/t-butyl methyl ether 2:1 containing 0.5% TEA) indicated the completion of the reaction. Pyridine rotoevaporated to dryness, residue was dissolved in ethyl acetate (250 mL) and washed successively with water (2×100 mL), saturated NH$_4$Cl solution (2×100 mL), brine (2×100 mL) and water (2×100 mL). Ethyl acetate layer dried over anhydrous MgSO$_4$ and rotoevaporated to dryness. The residue was purified on silica gel flash column chromatography using hexane/t-butyl methyl ether (3:1) containing 0.5% triethylamine to give bis-DMT product 2 as a white foam (2.9 g, 78%). $^1$H-NMR (CDCl3, 400 MHz): δ1.56 (s, 3H—CH$_3$), 1.74-1.79 (m, 4H, —CH$_2$CHCH$_2$—), 3.19-3.26 (m, 4H, 1 & 5-CH$_2$—), 3.78 (d, 12H, —OCH$_3$), 6.82 (dd, J=8.8, 8H, Ar—H), 7.16-7.40 (m, 18H, Ar—H).

Preparation of bis-DMT-3-methyl-pentanetriol derivatized CPG (5): LCAA-CPG (5 g) was added to 3% TCA in DCM (50 mL) and slowly agitated at room temperature for 3 h. The CPG was filtered and washed with 9:1 mixture of TEA/DIPEA (50 mL) followed by DCM (5×100 ml). The activated CPG dried under high vacuum for 1 h. A solution of succinic anhydride (1 g, 10 mmol) and DMAP (0.2 g) in pyridine (30 mL) was added to the above CPG (5 g) and the slurry was shaken at room temperature for 24 hrs. Solutions filtered off and CPG was washed with pyridine (2×25 mL) followed by DCM (5×25 mL) and dried under high vacuum for 2 h to obtain the succinic acid derivative of CPG 4. A solution of di-DMT-3-methyl-pentanetriol 2 (87 mg), DMAP (30 mg), TEA (100 μL) and DEC (0.4 g) in dry pyridine (10 mL) was added to CPG 4 and shaken at room temperature for 15 h. Pentachlorophenol (0.14 g) added to the above mixture and shaken for additional 15 hrs. Solutions filtered off, CPG was thoroughly washed with pyridine (2×25 mL) followed by DCM (5×25 mL) and dried under high vacuum in a desiccator for over night to get Di-DMT-3-methyl-pentanetriol derivatized CPG 5. Loading was determined by treating small portion of CPG with 3% TCA in DCM and assayed DMT content 37 μmol/g) by measuring absorbance at 498 mm.

Synthesis of pentane-1,3,5-triol (7): Diethyl 3-hydroxy glutarate (6, 25 g, 122.4 mmol) in THF (100 mL) was added dropwise to a 1M solution of LiAlH$_4$ in THF (400 mL) at 0° C. under argon atmosphere with vigorous stirring. After addition, reaction mixture was allowed to reach r. t. (~4 h) and stirred for overnight. The reaction mixture was cooled to −78° C. (acetone/dry ice bath) and quenched by dropwise addition of saturated NH$_4$Cl solution (50 mL) giving white precipitate. The reaction mixture was diluted with another 500 mL of THF and white precipitate was filtered through Celite. The precipitate was treated with boiling THF (250 mL) and filtered. The combined organic solution was dried over anhydrous MgSO$_4$ and solvent removed by rotoevaporation. The residue was purified on a silica gel flash column chromatography using DCM/EtOAc/methanol (6:3:1) affording triol 7 (11.4 g, 95.5 mmol, 78%) as a colorless oil. %). $^1$H-NMR (DMSO-d$_6$, 400 MHz): δ 1.39-1.54 (m, 4H, —CH$_2$CH(OH)CH$_2$—), 3.47 (t, J=6.6, 4H, 1 & 5-CH$_2$—), 3.61-3.68 (m, 1H, —CH(HO)—) and 4.23 (bs, 3H, 1, 3 & 5-OH).

1,5-Bis-[(4,4-dimethoxyphenyl)-phenylmethoxy]-pentan-3-ol (8). DMTCl (16.6 g, 49 mmol, 2.1 equiv) in pyridine (100 mL) was added dropwise to an ice cold (0° C.) and stirring solution of pentanetriol 7 (2.8 g, 23 mmol) and DMAP (2.85 g, 1 equiv) in dry pyridine (50 mL) under argon atmosphere. The reaction mixture was allowed to slowly reach r. t. (~4 h) and continued stirring for overnight. TLC (hexanes/EtOAc 3:1 containing 0.5% TEA) indicated the completion of the reaction. Pyridine rotoevaporated to dryness, residue was dissolved in DCM (500 mL) and washed successively with water (500 mL), saturated NH$_4$Cl solution (500 mL), brine (500 mL) and water (2×500 mL). DCM layer dried over anhydrous MgSO$_4$ and rotoevaporated to dryness. The residue was purified on silica gel flash column chromatography using hexane/EtOAc (3:1) containing 0.5% TEA to give bis-DMT alcohol 8 as a white foam (12.1 g, 16.7 mmol, 72%). $^1$H-NMR (CDCl3, 400 MHz): δ 1.65-1.81 (m, 4H, —CH$_2$CHCH$_2$—), 3.16-3.31 (m, 4H, DMTO-CH$_2$—), 3.78 (s, 12H, —OCH$_3$), 3.95-4.01 (m, 1H, —CH—), 6.81 (d, J=8.8, 8H, Ar—H), 7.17-7.42 (m, 18H, Ar—H). $^{13}$C NMR (CDCl3, 75.5 MHz): 37.22, 55.38, 61.81, 69.58, 86.54, 113.27, 126.88, 128.01, 128.26, 130.15, 136.44, 145.16, 158.55.

3(1,5-O-Dimethoxytrityl pentanetriol)succinic acid (9): bis-DMT alcohol 8 (12 g, 16.6 mmol) and DMAP (4.04 g, 33.2 mmol) were dissolved in dry pyridine (150 mL) and succinic anhydride (3.31 g, 33.2 mmol) was added portion wise at r.t. with vigorous stirring. The reaction mixture was stirred for over night and pyridine rotoevaporated to dryness. Residue was dissolved in DCM (500 mL) and successively washed with ice cold 10% citric acid solution (2×500 mL) and water (2×500 mL). DCM layer was dried over anhydrous MgSO$_4$, concentrated to 50 mL volume using rotoevaporator and purified by silica gel flash column chromatography using 0→2% methanol in DCM containing 0.5% TEA to get pure triethylammonium salt of succinate 9 as white foam (11.4 g, 13.8 mmol, 83%). $^1$H-NMR (CDCl3, 400 MHz): δ 1.20 (t, J=7.6, 9H, —N(CH$_2$CH$_3$)$_3$), 1.80-1.85 (m, 4H, —CH$_2$CHCH$_2$—), 2.40 (s, 4H, —COCH$_2$CH$_2$CO—), 2.90 (q, 6H, —N(CH$_2$CH$_3$)$_3$), 3.03-3.11 (m, 4H, 1 & 5-CH$_2$—), 3.78 (s, 12H, —OCH$_3$), 5.20-5.26 (m, 1H, —CH—), 6.81 (d, J=8.8, 8H, Ar—H), 7.17-7.42 (m, 18H, Ar—H). $^{13}$C NMR (CDCl3, 75.5 MHz): 9.09, 30.94, 31.77, 34.45, 45.08, 52.92, 55.32, 59.73, 69.73, 86.00, 113.12, 126.71, 127.85, 128.32, 130.11, 136.54, 145.22, 158.40, 173.07 and 177.71.

Preparation of bis-DMT pentanetriol loaded CPG (10): A solution of succinate 9 (0.83 g, 1 mmol), DMAP (0.4 g, 3.3 mmol) and DIC (5 mL) in 1:6 mixture of pyridine/acetonitrile (105 mL) was added to CPG (25 g) and the slurry was shaken for 24 hrs. Solutions filtered off and CPG was washed with acetonitrile containing 5% pyridine (100 mL) and acetonitrile (250 mL). Cap A (ABI, 89 mL) and Cap B (ABI, 100 mL) solutions were added to CPG support and shaken for 4 h. Solutions filtered off, CPG washed with acetonitrile containing 5% pyridine (2×100 mL) followed by acetonitrile (2×250 mL) and dried under high vacuum for 30 min. A solution of TBDMSCl (5.6 g) and imidazole (1.4 g) in acetonitrile containing 5% pyridine (150 mL) was added to CPG and shaken for 4 h. Solution filtered off, CPG was successively washed with acetonitrile containing 5% pyridine (3×100 mL) and DCM (4×250 mL) and dried under high vacuum in a desiccator for over night to get dry CPG support 10. Loading was determined by treating small portion of CPG with 3% TCA in DCM and assayed DMT content 40 μmol/g) by measuring absorbance at 498 mm.

Preparation of bis-DMT pentanetriol loaded OligoPrep250 (11): OligoPrep250 (100 g preswollen in acetonitrile) was taken in a peptide synthesis vessel and washed with anhydrous acetonitrile (3×100 mL). Succinate 9 (1.752 g, 2.125 mmol), DMAP (1.82 g, 14.87 mmol), TBTU (3.41 g, 10.62 mmol) and acetonitrile (100 mL) were added to Oligo- Prep250 and the slurry was shaken for 4 hrs. Solution filtered off and OligoPrep was washed with acetonitrile containing 1% TEA (2×100 mL) and acetonitrile (5×100 mL). Cap A (50 mL: NMI/pyridine/acetonitrile=2:3:5) and Cap B (50 mL: acetic anhydride/acetonitrile=1:4) solutions were added to solid support and shaken for 6 hrs. Solutions filtered off, solid support washed with acetonitrile (2×100 mL) and repeated the capping reaction one more time. Solutions filtered off, solid support washed with acetonitrile containing 1% TEA (3×100 mL) followed by acetonitrile (5×100 mL) and dried under high vacuum in a desiccator for 24 hrs to get dry OligoPrep250 support 11 (26.4 g). Loading was determined by treating small portion of OligoPrep with 3% TCA in DCM and assayed DMT content (138 µmol/g) by measuring absorbance at 498 mm.

5-Dimethoxytrityloxy-Pentane-1-ol (13): Pentanediol 12 (12.5 g, 120 mmol) and DMAP (14.6 g, 120 mmol) were dissolved in dry pyridine (100 mL), cooled to −10° C. and maintained under argon atmosphere. DMTCl (37.3 g, 110 mmol, 0.92 equiv) in pyridine (150 mL) was added drop wise with vigorous stirring. The reaction mixture was allowed to slowly reach r.t. (~4 h) and continued stirring for overnight. Pyridine rotoevaporated to dryness, residue dissolved in DCM (500 mL) and successively washed with water (250 mL), saturated $NH_4Cl$ solution (2×250 mL), brine (250 mL) and water (2×250 mL). DCM layer dried over anhydrous $MgSO_4$ and rotoevaporated to dryness. The residue was purified by silica gel flash column chromatography using hexanes/EtOAc (3:1) containing 0.5% TEA to give mono-DMT protected alcohol 13 as a colorless syrup (28.2 g, 58%). $^1$H-NMR (CDCl3, 400 MHz): δ 1.39-1.47 (m, 2H, —$CH_2CH_2CH_2OH$), 1.49-1.1.56 (m, 2H, DMTO-$CH_2CH_2$—), 1.60-1.68 (m, 2H, —$CH_2CH_2OH$), 3.06 (t, 2H, J=6.2, DMTO-$CH_2$—), 3.60 (t, 2H, J=6.3, —$CH_2OH$), 3.77 (s, 12H, —$OCH_3$), 6.82 (d, J=8.8, 8H, Ar—H), 7.17-7.45 (m, 18H, Ar—H). $^{13}$C NMR (CDCl3, 75.5 MHz): 22.84, 30.14, 32.92, 55.51, 63.21, 63.57, 85.98, 113.26, 126.87, 128.00, 128.46, 130.30, 136.96, 145.65 and 158.57.

5-Dimethoxytrityloxy-Pentane-1-O-(2-cyanoethyl-N,N-diisopropyl)phosphoramidite (14): To an ice cold solution of 13 (20.32 g, 50 mmol) in anhydrous DCM (500 mL) under nitrogen atmosphere was added DIPEA (26.12 mL, 150 mmol) with vigorous stirring. 2-Cyanoethyl-N,N-diisopropylchlorophosphoramidite (14.2 g, 60 mmol) was then added dropwise followed by NMI (4 mL, 50 mmol). The reaction mixture allowed to slowly reach r.t. in ~4 h and continued stirring for overnight. TLC in 3:1 hexanes/EtOAc containing 0.5% TEA exhibited the completion of the reaction. The reaction mixture was diluted with another 500 mL of DCM and washed sequentially with saturated aqueous $NaHCO_3$ (1×500 mL), brine (2×500 mL) and water (1×500 mL). The organic layer dried over anhydrous $MgSO_4$, filtered and rotoevaporated to dryness. The residue was purified on silica gel flash column chromatography using 3:1 hexane/EtOAc mixture containing 0.5% TEA to get 13 as a colorless viscous liquid (22.3 g, 74%). $^1$H-NMR (CDCl3, 400 MHz): δ 1.15 (t, 12H, J=7.6, ($Me_2CH)_2N$—), 1.37-1.45 (m, 2H, —$CH_2CH_2CH_2OP$—), 1.52-1.64 (m, 4H, DMTO-$CH_2CH_2CH_2CH_2$—), 2.55 (t, 2H, J=6.2, —$CH_2CN$), 3.01 (t, 2H, J=6.5, —$CH_2CH_2CN$), 3.49-3.64 (m, 4H, DMTO-$CH_2$— and —$CH_2OP$—), 3.73 (s, 12H, —$OCH_3$), 3.71-3.81 (m, 2H, ($Me_2CH)_2N$—), 6.77 (d, J=8.8, 8H, Ar—H), 7.13-7.41 (m, 18H, Ar—H). $^{13}$C NMR (CDCl3, 75.5 MHz): 20.56, 20.63, 23.08, 24.82, 24.89, 24.96, 30.05, 31.40, 43.15, 43.27, 55.46, 58.47, 58.66, 63.52, 63.92, 85.89, 113.20, 117.97, 126.81, 127.94, 128.42, 130.25, 136.92, 145.65 and 158.53. $^{31}$P-NMR: δ145.07.

Synthesis of phosphoramidites 15 and 16: Synthesized using general procedure as described for 14. Compound 15—white foam and yield 69%. $^1$H-NMR (CDCl3, 400 MHz): δ 0.89 (d, 6H, J=7, ($Me_2CH)_2N$—), 1.05 (d, 6H, J=6.4, ($Me_2CH)_2N$—), 1.25 (s, 3H, —$CH_3$), 1.88-1.99 (m, 4H, —$CH_2CHCH_2$—), 2.40 (t, 2H, J=6.4, —$CH_2CN$), 3.10-3.21 (m, 2H, —$OCH_2CH_2CN$), 3.30-3.40 (m, 2H, $Me_2CH)_2N$—), 3.43-3.60 (m, 4H, DMTO-$CH_2$—), 3.77 (d, 12H, —$OCH_3$), 6.79 (dd, J=8.8, 8H, Ar—H), 7.17-7.42 (m, 18H, Ar—H). $^{13}$C NMR (CDCl3, 75.5 MHz): 20.39, 24.27, 24.72, 43.03, 55.38, 57.73, 60.23, 77.96, 78.04, 86.28, 113.15, 118.01, 126.74, 127.89, 128.31, 129.31, 130.18, 136.80, 139.62, 145.47, 158.44. $^{31}$P-NMR: δ 135.93.

Compound 16—white foam and yield 79%. $^1$H-NMR (CDCl3, 400 MHz): δ 1.00 (d, 6H, J=6.4, ($Me_2CH)_2N$—), 1.10 (d, 6H, J=6.7, ($Me_2CH)_2N$—), 1.73-1.99 (m, 4H, DMTO-$CH_2CH_2CHCH_2$—), 2.36 (t, 2H, J=6.6, —$CH_2CN$), 3.14 (t, 2H, J=6.5, —$CH_2CH_2CN$), 3.37-3.60 (m, 6H, DMTO-$CH_2$— and $Me_2CH)_2N$—), 3.77 (d, 12H, —$OCH_3$), 4.14-4.22 (m, 1H, —CHOP—), 6.78 (dd, J=8.8, 8H, Ar—H), 7.17-7.42 (m, 18H, Ar—H). $^{13}$C NMR (CDCl3, 75.5 MHz): 20.38, 24.56, 24.88, 36.82, 43.08, 55.43, 58.39, 60.45, 69.88, 86.09, 113.18, 117.88, 126.81, 127.93, 128.36, 130.20, 136.77, 137.59, 145.47, 158.49. $^{31}$P-NMR: δ 145.20.

cis-3,5-Bis-dimethoxytrityloxy-cyclohexane-1-ol (18). cis-1,3,5-Cyclohexanetriol dehydrate (5.05 g, 30 mmol) was dissolved in pyridine (100 mL) and rotoevaporated to dryness and dried under high vacuum for 48 hrs to obtain anhydrous cis-1,3,5-cyclohexanetriol (4.05 g, 30.6 mmol). The above anhydrous cyclohexanetriol and DMAP (7.33 g, 60 mmol) were dissolved in dry pyridine (100 mL), cooled in ice bath and maintained under nitrogen atmosphere. DMTCl (20.4 g, 60 mmol, 2 equiv) in dry pyridine (150 mL) was added drop wise to the above solution with vigorous stirring. The reaction mixture was allowed to slowly reach r.t. (~4 h) and continued stirring for 24 hrs. TLC in 2:1 hexanes/EtOAc mixture containing 0.5% TEA indicated the presence of some starting materials. Reaction mixture stirred five more hrs at 60° C. and pyridine rotoevaporated to dryness. The residue was dissolved in DCM (500 mL) and washed successively with water (500 mL), saturated $NH_4Cl$ solution (500 mL), brine (500 mL) and water (2×500 mL). DCM layer dried over anhydrous $MgSO_4$ and rotoevaporated to dryness. The residue was purified on silica gel flash column chromatography using 3:1 hexane/EtOAc mixture containing 0.5% TEA to give bis-DMT product 18 as a white solid (8.4 g, 38%). $^1$H-NMR (CDCl3, 400 MHz): δ 1.04-1.13 (m, 3H, 2, 4 & 6-$CH_2$—), 1.24-1.28 (m, 3H, 2, 4 & 6-$CH_2$—), 1.66 (d, 1H, 1-OH), 2.84-2.93 (m, 1H, —CH—OH), 3.10-3.18 (m, 2H, 3 & 5-CH—), 3.78 (d, 12H, —$OCH_3$), 6.78 (d, J=8.8, 8H, Ar—H), 7.16-7.42 (m, 18H, Ar—H). $^{13}$C NMR (CDCl3, 75.5 MHz): 41.42, 42.67, 55.37, 66.16, 67.91, 86.28, 113.12, 126.83, 127.81, 128.53, 130.41, 137.39, 146.29, 158.53.

1(3,5-bis-Dimethoxytrityl-cis-cyclohexanetriol)succinic acid (19): bis-DMT-cyclohexanetriol 18 (4.05 g, 5.5 mmol) and DMAP (1.34 g, 10.1 mmol) were dissolved in dry pyridine (50 mL) and succinic anhydride (1.1 g, 10.1 mmol) was added portion wise at r.t. with vigorous stirring. The reaction mixture was stirred for 48 hrs at r.t. and TLC in DCM containing 2% methanol and 0.5% TEA indicated the complete disappearance of starting material. Pyridine rotoevaporated to dryness, residue dissolved in DCM (250 mL) and successively washed with ice cold 10% citric acid solution (2×250 mL) and water (2×250 mL). DCM layer dried over anhydrous $MgSO_4$, concentrated to 50 mL volume using rotoevaporator and purified by silica gel flash column chromatography using 0→2% methanol in DCM containing 0.5% TEA to get pure triethylammonium salt of succinate 19 as white foam (3.58 g, 78%). $^1$H-NMR (CDCl3, 400 MHz δ 1.17 (t, J=7.6, 9H, —N(CH$_2$CH$_3$)$_3$), 1.17-1.25 (m, 2H, 4-CH$_2$—), 1.36-1.51 (m, 4H, 2 & 6-CH$_2$—), 2.37-2.47 (m, 4H, —OCH$_2$CH$_2$CN), 2.86 (q, 6H, —N(CH$_2$CH$_3$)$_3$), 2.99-3.10 (m, 2H, 3 & 5-CH—), 3.78 (d, 12H, —OCH$_3$), 3.98-4.08 (m, 1H, 1-CH—), 6.76 (dd, J=8.8, 8H, Ar—H), 7.15-7.37 (m, 18H, Ar—H). $^{13}$C NMR (CDCl3, 75.5 MHz): 9.38, 31.16, 31.96, 39.02, 41.76, 45.18, 55.37, 67.68, 86.24, 113.12, 126.79, 127.77, 128.42, 130.33, 130.38, 137.15, 137.26, 146.28, 158.54, 172.58 and 178.16.

Preparation of bis-DMT cyclohexanetriol derivatized CPG 20: A solution of succinate 19 (0.78 g, 0.93 mmol), DMAP (0.38 g, 2.8 mmol) and DIC (3 mL) in 1:7.5 mixture of pyridine/acetonitrile (85 mL) was added to CPG (22.5 g) and the slurry was agitated for 24 hrs. Solutions filtered off and CPG was washed with acetonitrile containing 5% pyridine (2×100 mL) and acetonitrile (3×100 mL). Cap A (ABI, 80 mL) and Cap B (ABI, 90 mL) solutions were added to CPG support and shaken for 4 h. Solutions filtered off, CPG washed with acetonitrile containing 5% pyridine (2×100 mL) followed by acetonitrile (2×250 mL) and dried under high vacuum for 30 min. A solution of TBDMSCl (2.5 g) and imidazole (0.75 g) in acetonitrile containing 5% pyridine (100 mL) was added to CPG and shaken for 5 h. Solution filtered off, CPG was successively washed with acetonitrile containing 5% pyridine (3×100 mL) and DCM (4×100 mL) and dried under high vacuum in a desiccator for over night to get dry CPG support 20. Loading was determined by treating small portion of CPG with 3% TCA in DCM and assayed DMT content 40 μmol/g) by measuring absorbance at 498 mm.

EXAMPLE 2

Cell Culture Conditions and Reagents, Cytokine Induction by Exemplar Oligos from Table I in HEK293 Cells Expressing Mouse TLR9

HEK293 cells stably expressing mouse TLR9 (Invivogen, San Diego, Calif.) were cultured in 48-well plates in 250 μl/well DMEM supplemented with 10% heat-inactivated FBS in a 5% CO$_2$ incubator. At 80% confluence, cultures were transiently transfected with 400 ng/ml of SEAP (secreted form of human embryonic alkaline phosphatase) reporter plasmid (pNifty2-Seap) (Invivogen) in the presence of 4 μl/ml of lipofectamine (Invitrogen, Carlsbad, Calif.) in culture medium. Plasmid DNA and lipofectamine were diluted separately in serum-free medium and incubated at room temperature for 5 minutes. After incubation, the diluted DNA and lipofectamine were mixed and the mixtures were incubated at room temperature for 20 minutes. Aliquots of 25 μl of the DNA/lipofectamine mixture containing 100 ng of plasmid DNA and 1 μl of lipofectamine were added to each well of the cell culture plate, and the cultures were continued for 4 hours.

After transfection, medium was replaced with fresh culture medium, exemplar oligos from Table I were added to the cultures, and the cultures were continued for 24 hours. At the end of oligo treatment, 30 μl of culture supernatant was taken from each treatment and used for SEAP assay following manufacturer's protocol (Invivogen). Briefly, culture supernatants were incubated with p-nitrophenyl phosphate substrate and the yellow color generated was measured by a plate reader at 405 nm (Putta M R et al, Nucleic Acids Res., 2006, 34:3231-8).

EXAMPLE 3

Cytokine Induction by Exemplar Oligos from Table I in Human PBMCs, pDCs, and Mouse Splenocytes Human PBMC Isolation Peripheral blood mononuclear cells (PBMCs) from freshly drawn healthy volunteer blood (CBR Laboratories, Boston, Mass.) were isolated by Ficoll density gradient centrifugation method (Histopaque-1077, Sigma).

Human pDC Isolation pDCs were isolated from PBMCs by positive selection using the BDCA4 cell isolation kits (Miltenyi Biotec) according to the manufacturer's instructions.

Mouse Splenocyte Isolation

Spleen cells from 4-8 week old C57BL/6 mice were cultured in RPMI complete medium as described by Zhao, Q., et al (*Biochem Pharmacol*. 51: 173-182 (1996)) and Branda, R. F., et al (*Biochem. Pharmacol*. 45: 2037-2043 (1993)). All other culture reagents were purchased from Mediatech (Gaithersburg, Md.).

Cytokine ELISAs

Human PBMCs or mouse splenocytes were plated in 48-well plates using $5 \times 10^6$ cells/ml. Human pDCs were plated in 96-well dishes using $1 \times 10^6$ cells/ml. The exemplar oligos from Table I dissolved in DPBS (pH 7.4; Mediatech) were added to the cell cultures. The cells were then incubated at 37° C. for 24 hr and the supernatants were collected for luminex multiplex or ELISA assays. In certain experiments, the levels of IFN-α, IL-6, and/or IL-12 were measured by sandwich ELISA. The required reagents, including cytokine antibodies and standards, were purchased from PharMingen.

Cytokine Luminex Multiplex

In certain experiments, the levels of IL-1Rα, IL-6, IL-10, IL-12, IFN-α, IFN-γ, MIP-1α, MIP-β, MCP-1, and IL-12p40p70 in culture supernatants were measured by Luminex multiplex assays, which were performed using Biosource human multiplex cytokine assay kits on Luminex 100 instrument and the data were analyzed using StarStation software supplied by Applied Cytometry Systems (Sacramento, Calif.).

EXAMPLE 4

Human B Cell Proliferation Assay in the Presence of Exemplar Oligos from Table I Human B cells were isolated from PBMCs by positive selection using the CD19 Cell Isolation Kit (Miltenyi Biotec, Auburn, Calif.) according to the manufacturer's instructions.

The culture medium used for the assay consisted of RPMI 1640 medium supplemented with 1.5 mM glutamine, 1 mM sodium pyruvate, 0.1 mM non-essential amino acids, 50 μM 2-mercaptoethanol, 100 IU/ml penicillin-streptomycin mix and 10% heat-inactivated fetal bovine serum.

A total of $0.5 \times 10^6$ B cells per ml (i.e. $1 \times 10^5/200$ μl/well) were stimulated in 96 well flat bottom plates with different concentrations of exemplar oligos from Table I in triplicate for a total period of 72 hours. After 66 h, cells were pulsed with 0.75 μCi of [$^3$H]-thymidine (1Ci=37 GBq; Perkin Elmer Life Sciences) in 20 μl RPMI 1640 medium (no serum) per well and harvested 6-8 h later. The plates were then harvested using a cell harvester and radioactive incorporation was determined using standard liquid scintillation technique. In some cases the corresponding [$^3$H]-T (cpm) was converted into a proliferation index and reported as such.

What is claimed is:

1. A TLR9 agonist having an oligonucleotide comprising the structure 5'-TCAGTCG$_2$TTAC-X-CATTG$_2$CTGACT-5', wherein X is a glycerol linker and G$_2$ is arabinoguanosine, and wherein internucleoside linkages are selected from the group consisting of phosphodiester linkages, phosphorothioate linkages and mixtures thereof.

2. A composition comprising the TLR9 agonist according to claim 1 and a physiologically acceptable carrier.

3. A vaccine comprising the composition according to claim 2 and an antigen.

4. A method for generating a TLR9-mediated immune response in a vertebrate, comprising administering to the vertebrate an effective amount of the TLR9 agonist according to claim 1.

5. A method for generating a TLR9-mediated immune response in a vertebrate, comprising administering to the vertebrate an effective amount of the composition according to claim 2.

* * * * *